United States Patent
Kamp et al.

(10) Patent No.: US 11,072,780 B2
(45) Date of Patent: Jul. 27, 2021

(54) METHOD OF DIFFERENTIATING HUMAN PLURIPOTENT CELLS INTO CARDIAC FIBROBLASTS

(71) Applicant: Wisconsin Alumni Research Foundation, Madison, WI (US)

(72) Inventors: Timothy Joseph Kamp, Madison, WI (US); Jianhua Zhang, Madison, WI (US)

(73) Assignee: WISCONSIN ALUMNI RESEARCH FOUNDATION, Madison, WI (US)

(*) Notice: Subject to any disclaimer, the term of this patent is extended or adjusted under 35 U.S.C. 154(b) by 0 days.

(21) Appl. No.: 15/720,657

(22) Filed: Sep. 29, 2017

(65) Prior Publication Data
US 2018/0094245 A1    Apr. 5, 2018

Related U.S. Application Data

(60) Provisional application No. 62/402,694, filed on Sep. 30, 2016.

(51) Int. Cl.
| | | |
|---|---|---|
| *C12N 5/00* | (2006.01) | |
| *C12N 5/077* | (2010.01) | |
| *C12N 5/074* | (2010.01) | |
| *C12N 5/0735* | (2010.01) | |

(52) U.S. Cl.
CPC ......... *C12N 5/0657* (2013.01); *C12N 5/0606* (2013.01); *C12N 5/0607* (2013.01); *C12N 5/0656* (2013.01); C12N 2501/115 (2013.01); C12N 2501/415 (2013.01); C12N 2506/00 (2013.01); C12N 2506/02 (2013.01); C12N 2506/45 (2013.01); C12N 2533/90 (2013.01)

(58) Field of Classification Search
CPC .. C12N 5/0657; C12N 5/0606; C12N 5/0607; C12N 2506/00
USPC .................................................. 435/325, 455
See application file for complete search history.

(56) References Cited

U.S. PATENT DOCUMENTS

| | | | | |
|---|---|---|---|---|
| 8,017,389 B2* | 9/2011 | Phillips | ............... | C12N 5/0657 |
| | | | | 424/93.1 |
| 8,318,489 B2* | 11/2012 | Davidson | ............ | G01N 33/502 |
| | | | | 435/377 |
| 9,238,795 B2* | 1/2016 | Sinha | ................... | C12N 5/0661 |
| 2008/0254002 A1* | 10/2008 | Edelberg | ............... | A61K 35/28 |
| | | | | 424/93.7 |

FOREIGN PATENT DOCUMENTS

WO        1998/30679        7/1998

OTHER PUBLICATIONS

Shenje (eLIFE, 2013, vol. 3, e02164).*
Francou (Biochimica et Biophysica ACTA—Molecular Cell Research, Apr. 2013, vol. 1833, No. 4, p. 795-798).*

(Continued)

*Primary Examiner* — Michael C Wilson
(74) *Attorney, Agent, or Firm* — McDonnell Boehnen Hulbert & Berghoff LLP

(57) ABSTRACT

Methods for generating high-yield, high-purity cardiac fibroblasts are described. Differentiation methods comprising chemically defined culture conditions and methods for in vitro maintenance of human pluripotent stem cell-derived cardiac fibroblasts are also provided.

8 Claims, 29 Drawing Sheets
(27 of 29 Drawing Sheet(s) Filed in Color)

(56) References Cited

OTHER PUBLICATIONS

Zhao ("Efficient differentiation of TBX18+/WT1+ epicardial-like cells from human pluripotent stem cells using small molecular compounds." Stem Cells Dev 2017;26(7):528-540.*
Witty "Generation of the epicardial lineage from human pluripotent stem cells." Nat Biotechnol. 2014;32(10): 1026-1035.*
Iyer ("Robust derivation of epicardium and its differentiated smooth muscle cell progeny from human pluripotent stem cells." Development. 2015; 142(8): 1528-1541.*
Kwon (The Scientist, Sep. 2018) taught "Adult cardiac stem cells don't exist: Study" (title).*
Kattman, Cell Stem Cell, 2011, vol. 8, p. 228-240.*
Lian, Nat. Protoc., 2013, vol. 8, p. 162-175.*
D'Souza, K.M. et al. G protein-coupled receptor kinase-2 is a novel regulator of collagen synthesis in adult human cardiac fibroblasts. J Biol Chem 286, 15507-15516 (2011) Withdrawn.
Spater, D. et al. A HCN4+ cardiomyogenic progenitor derived from the first heart field and human pluripotent stem cells. Nat Cell Biol 15, 1098-1106 (2013).
Thomson et al., Embryonic Stem Cell Lines Derived from Human Blastocysts, Science 282:1145-1147 (1998).
Tsuchihashi, T. et al. Hand2 function in second heart field progenitors is essential for cardiogenesis. Dev Biol 351, 62-69 (2011).
Urness, et al., Redundant and dosage sensitive requirements for Fgf3 and Fgf10 in cardiovascular development, Developmental Biology, vol. 356, Issue 2, Aug. 15, 2011, pp. 383-397.
Van Wijk, B. et al. Epicardium and myocardium separate from a common precursor pool by crosstalk between bone morphogenetic protein- and fibroblast growth factor-signaling pathways. Circ Res 105, 431-441 (2009).
Villarejo, A., Cortes-Cabrera, A., Molina-Ortiz, P., Portillo, F. & Cano, A. Differential role of Snail1 and Snail2 zinc fingers in E-cadherin repression and epithelial to mesenchymal transition. J Biol Chem 289, 930-941 (2014).
Vliegen et al., Myocardial changes in pressure overload-induced left ventricular hypertrophy. A study on tissue composition, polyploidization and multinucleation, European Heart Journal, Apr. 1, 1991, 12(4):488-494.
Vodyanik, M.A. et al. A mesoderm-derived precursor for mesenchymal stem and endothelial cells. Cell Stem Cell 7, 118-729 (2010).
Watanabe, et al., Role of Mesodermal FGF8 and FGF10 Overlaps in the Development of the Arterial Pole of the Heart and Pharyngeal Arch Arteries, Circulation Research. 2010;106:495-503.
Wessels, A. et al. Epicardially derived fibroblasts preferentially contribute to the parietal leaflets of the atrioventricular valves in the murine heart. Dev Biol 366, 111-124 (2012).
Witty, et al., Generation of the epicardial lineage from human pluripotent stem cells. Nat Biotechnol 32, 1026-1035 (2014).
Xu, H. et al. Tbx1 has a dual role in the morphogenesis of the cardiac outflow tract. Development 131, 3217-3227 (2004).
Yang, et al., Human cardiovascular progenitor cells develop from a Kdr+ embryonic-stem-cell-derived population. Nature 453, 524-528 (2008).
Yu, et al., Human induced pluripotent stem cells free of vector and transgene sequences, Science 324(5928):797-801 (2009).
Yu, et al., Induced pluripotent stem cell lines derived from human somatic cells, Science 318:1917-1920 (2007).
Zaitsev, et al., Distribution of excitation frequencies on the epicardial and endocardial surfaces of fibrillating ventricular wall of the sheep heart. Circ Res 86, 408-417 (2000).
Zeisberg, et al. Origins of cardiac fibroblasts. Circ Res 107, 1304-1312 (2010).
Zeng, et al., Apelin and its receptor control heart field formation during zebrafish gastrulation. Developmental cell 12, 391-402 (2007).
Zhang, et al. Extracellular matrix promotes highly efficient cardiac differentiation of human pluripotent stem cells: the matrix sandwich method. Circ Res 111, 1125-1136 (2012).
Zhang, et al., Functional Cardiomyocytes Derived From Human Induced Pluripotent Stem Cells, Circulation Research. 2009;104:e30-e41.
Acharya, et al. The bHLH transcription factor Tcf21 is required for lineage-specific EMT of cardiac fibroblast progenitors. Development 139, 2139-2149 (2012).
Ali, S.R. et al. Developmental heterogeneity of cardiac fibroblasts does not predict pathological proliferation and activation. Circ Res 115, 625-635 (2014).
Anversa, et al., Stereological Measurement of Cellular and Subcellular Hypertrophy and Hyperplasia in the Papillary Muscle of Adult Rat, J. Molecular Cell. Cardiology 12(8):781-795, 1980.
Baba, et al., Constitutively Active β-Catenin Confers Multilineage Differentiation Potential on Lymphoid and Myeloid Progenitors (2005), Immunity 23(6):599-609.
Banerjee, et al., Determination of cell types and numbers during cardiac development in the neonatal and adult rat and mouse, Am. J. Physiol.—Heart and Circulatory Physiology 293(3):H1883-H1891, 2007.
Bergmann, et al., Dynamics of Cell Generation and Turnover in the Human Heart, Cell 161(7):1566-1575, 2015.
Brown, et al., The cardiac fibroblast: therapeutic target in myocardial remodeling and failure. Annu Rev Pharmacol Toxicol 45, 657-687 (2005).
Bruneau, B.G. et al. Chamber-specific cardiac expression of Tbx5 and heart defects in Holt-Oram syndrome. Dev Biol 211, 100-108 (1999).
Bu, L. et al. Human ISL1 heart progenitors generate diverse multipotent cardiovascular cell lineages. Nature 460, 113-117 (2009).
Cai, C.L. et al. A myocardial lineage derives from Tbx18 epicardial cells. Nature 454, 104-108 (2008).
Cai, C.L. et al. Isl1 identifies a cardiac progenitor population that proliferates prior to differentiation and contributes a majority of cells to the heart. Dev.Cell 5, 877-889 (2003).
Camelliti, et al., Structural and functional characterisation of cardiac fibroblasts. Cardiovasc Res 65, 40-51 (2005).
Campbell et al., Spatial gradients in action potential duration created by regional magnetofection of hERG are a substrate for wavebreak and turbulent propagation in cardiomyocyte monolayers 2012 J Physiol, 590(24):6363-79.
Chen et al., Chemically defined conditions for human iPS cell derivation and culture, Nat. Methods 8(5):424-9 (2011).
Cohen, et al., Wnt/β-catenin signaling promotes expansion of Isl-1-positive cardiac progenitor cells through regulation of FGF signaling, J Clin Invest Jul. 2, 2007; 117(7): 1794-1804.
Creemers, et al., Genome-Wide Polyadenylation Maps Reveal Dynamic mRNA 3'-End Formation in the Failing Human Heart, Circ. Res. 118(3) 2016.
D'Aniello, C. et al. G protein-coupled receptor APJ and its ligand apelin act downstream of Cripto to specify embryonic stem cells toward the cardiac lineage through extracellular signal-regulated kinase/p70S6 kinase signaling pathway. Circ Res 105, 231-238 (2009).
Ebert et al., Induced pluripotent stem cells from a spinal muscular atrophy patient, Nature 457(7227):277-80 (2009).
Furtado, M.B. et al. Cardiogenic genes expressed in cardiac fibroblasts contribute to heart development and repair. Circ Res 114, 1422-1434 (2014).
Hagen et al., Expression and Characterization of GSK-3 Mutants and Their Effect on β-Catenin Phosphorylation in Intact Cells, (2002), J Biol Chem, 277(26):23330-23335.
Herron, et al. Extracellular Matrix-Mediated Maturation of Human Pluripotent Stem Cell-Derived Cardiac Monolayer Structure and Electrophysiological Function. Circulation. Arrhythmia and electrophysiology 9, e003638 (2016).
Hou et al., A Major Role for hERG in Determining Frequency of Reentry in Neonatal Rat Ventricular Myocyte Monolayer, 2010 Circ Res., 107(12):1503-11.
Howden et al., Genetic correction and analysis of induced pluripotent stem cells from a patient with gyrate atrophy, Proc. Natl. Acad. Sci. U. S. A. 108(16):6537-42 (2011).

(56) References Cited

OTHER PUBLICATIONS

Ieda, M. et al. Cardiac fibroblasts regulate myocardial proliferation through beta1 integrin signaling. Developmental cell 16, 233-244 (2009).

Ilagan, et al., Fgf8 is required for anterior heart field development, Development 133, 2435-2445 (2006).

Kaaya, E.E. et al. Heterogeneity of spindle cells in Kaposi's sarcoma: comparison of cells in lesions and in culture. J Acquir Immune Defic Syndr Hum Retrovirol 10, 295-305 (1995).

Kattman, S.J. et al. Stage-specific optimization of activin/nodal and BMP signaling promotes cardiac differentiation of mouse and human pluripotent stem cell lines. Cell Stem Cell 8, 228-240 (2011).

Kelly RG, The second heart field, Curr Topics Dev Biol 100:33-65, 2012.

Kleber et al., Basic Mechanisms of Cardiac Impulse Propagation and Associated Arrhythmias, Physiol Rev. 2004, 84(2):431-88).

Kohl, P. & Gourdie, R.G. Fibroblast-myocyte electrotonic coupling: does it occur in native cardiac tissue? J Mol Cell Cardiol 70, 37-46 (2014).

Lajiness & Conway, The Dynamic Role of Cardiac Fibroblasts in Development and Disease, J Cardiovasc Transl Res. Dec. 2012; 5(6): 739-748.

Langmead, et al., Ultrafast and memory-efficient alignment of short DNA sequences to the human genome. Genome Biol 10, R25 (2009).

Lee, P. et al. Single-sensor system for spatially resolved, continuous, and multiparametric optical mapping of cardiac issue. Heart Rhythm 8, 1482-1491 (2011).

Li, B. & Dewey, C.N. RSEM: accurate transcript quantification from RNA-Seq data with or without a reference genome. BMC Bioinformatics 12, 323 (2011).

Lian, et al. Directed cardiomyocyte differentiation from human pluripotent stem cells by modulating Wnt/beta-catenin signaling under fully defined conditions. Nat Protoc 8, 162-175 (2013).

Lian, et al. Robust cardiomyocyte differentiation from human pluripotent stem cells via temporal modulation of canonical Wnt signaling. Proceedings of the National Academy of Sciences of the United States of America 109, E1848-1857 (2012).

Lin, et al., β-Catenin directly regulates Islet1 expression in cardiovascular progenitors and is required for multiple aspects of cardiogenesis, PNAS, May 29, 2007, vol. 104, No. 22, pp. 9313-9318.

Loh, K.M. et al. Mapping the Pairwise Choices Leading from Pluripotency to Human Bone, Heart, and Other Mesoderm Cell Types. Cell 166, 451-467 (2016).

Mikawa, et al., Pericardial mesoderm generates a population of coronary smooth muscle cells migrating into the heart along with ingrowth of the epicardial organ. Dev Biol 174, 221-232 (1996).

Moore-Morris, T. et al. Resident fibroblast lineages mediate pressure overload-induced cardiac fibrosis. J Clin Invest 124, 2921-2934 (2014).

Morley, et al. Characterization of conduction in the ventricles of normal and heterozygous Cx43 knockout mice using optical mapping. J Cardiovasc Electrophysiol 10, 1361-1375 (1999).

Nag, Studies of adult amphibian heart cells in Vitro: DNA synthesis and mitosis, Tissue & Cell 12(1):125-139, 1980.

Park, et al., An FGF autocrine loop initiated in second heart field mesoderm regulates morphogenesis at the arterial pole of the heart, Development, 2008, vol. 135, pp. 3599-3610.

Park, et al., Required, tissue-specific roles for Fgf8 in outflow tract formation and remodeling, Development 133, 2419-2433 (2006).

Porter, et al., Cardiac fibroblasts: at the heart of myocardial remodeling. Pharmacol Ther 123, 255-278 (2009).

Schmuck, et al., Cardiac fibroblast-derived 3D extracellular matrix seeded with mesenchymal stem cells as a novel device to transfer cells to the ischemic myocardium. Cardiovascular engineering and technology 5, 119-131 (2014).

Scott, et al., The g protein-coupled receptor agtrl1b regulates early development of myocardial progenitors. Developmental cell 12, 403-413 (2007).

Smith, et al., Epicardial-derived cell epithelial-to-mesenchymal transition and fate specification require PDGF receptor signaling. Circ Res 108, e15-26 (2011).

Snider, P. et al. Origin of cardiac fibroblasts and the role of periostin. Circ Res 105, 934-947 (2009).

Souders, C.A., Bowers, S.L. & Baudino, T.A. Cardiac fibroblast: the renaissance cell. Circ Res 105, 1164-1176 (2009).

MacDonald et al. "Wnt/β-catenin signaling: components, mechanism, and diseases," Dev. Cell., 2009.

\* cited by examiner

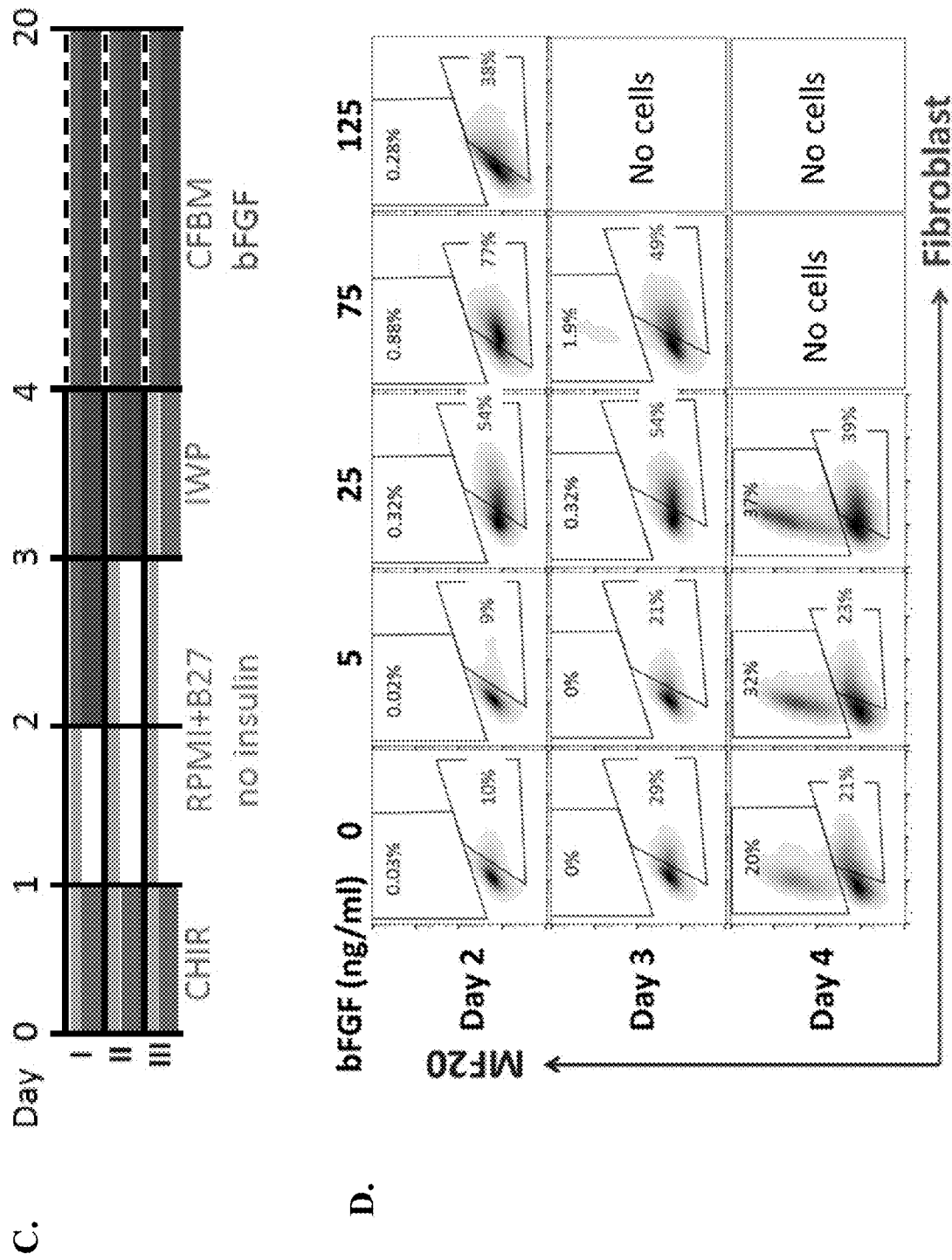
FIGS. 1A-1F, CONTINUED

FIGS. 1A-1F, CONTINUED
E.
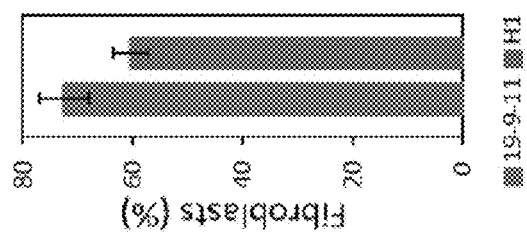
F.
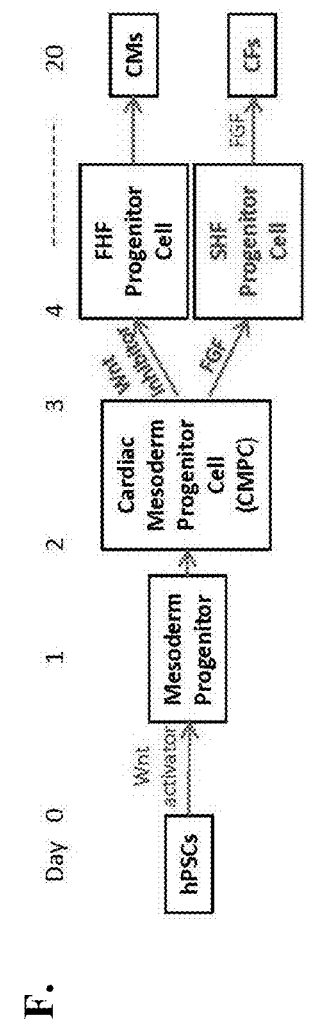

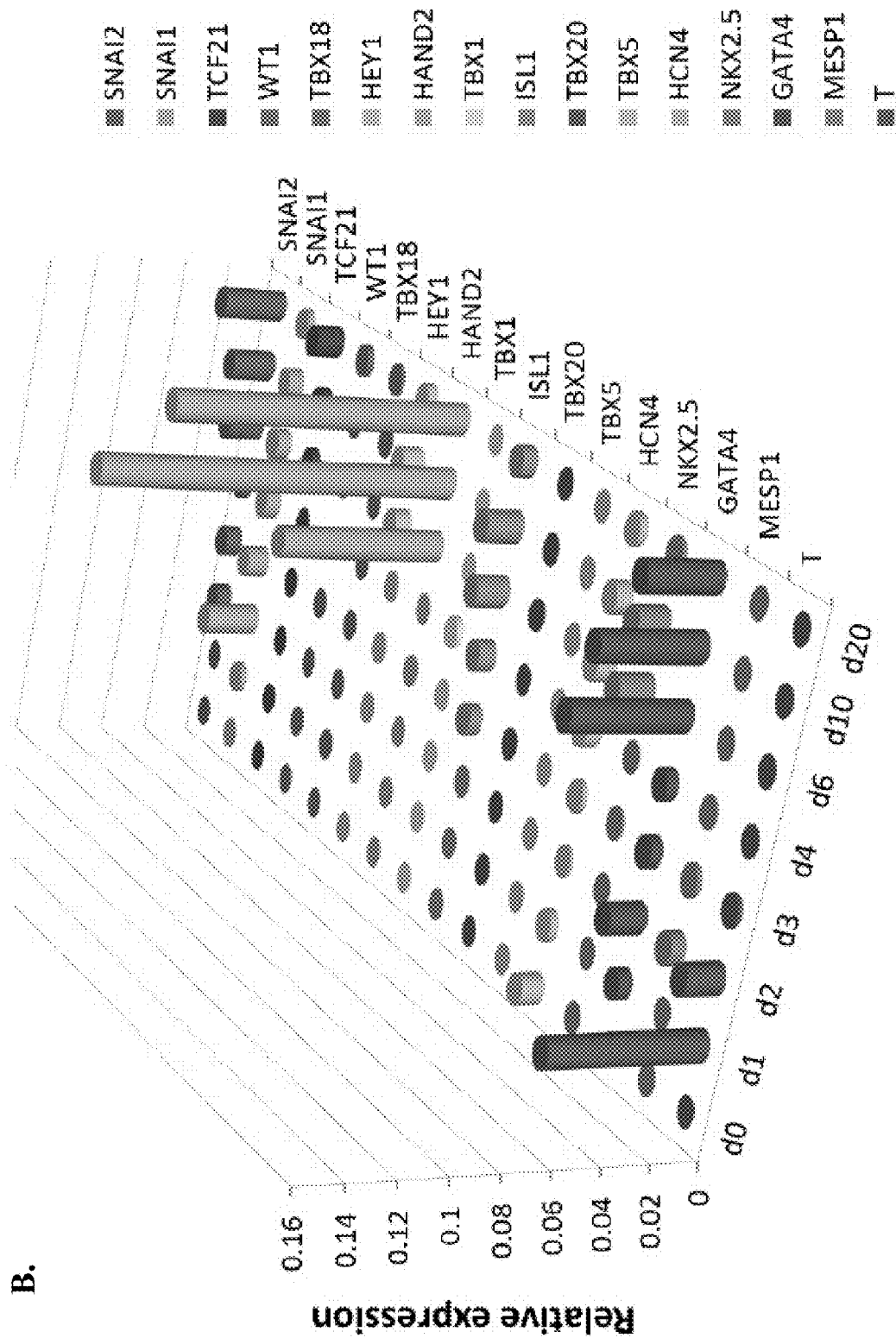
FIGS. 2A-2C, CONTINUED

FIGS. 2A-2C, CONTINUED
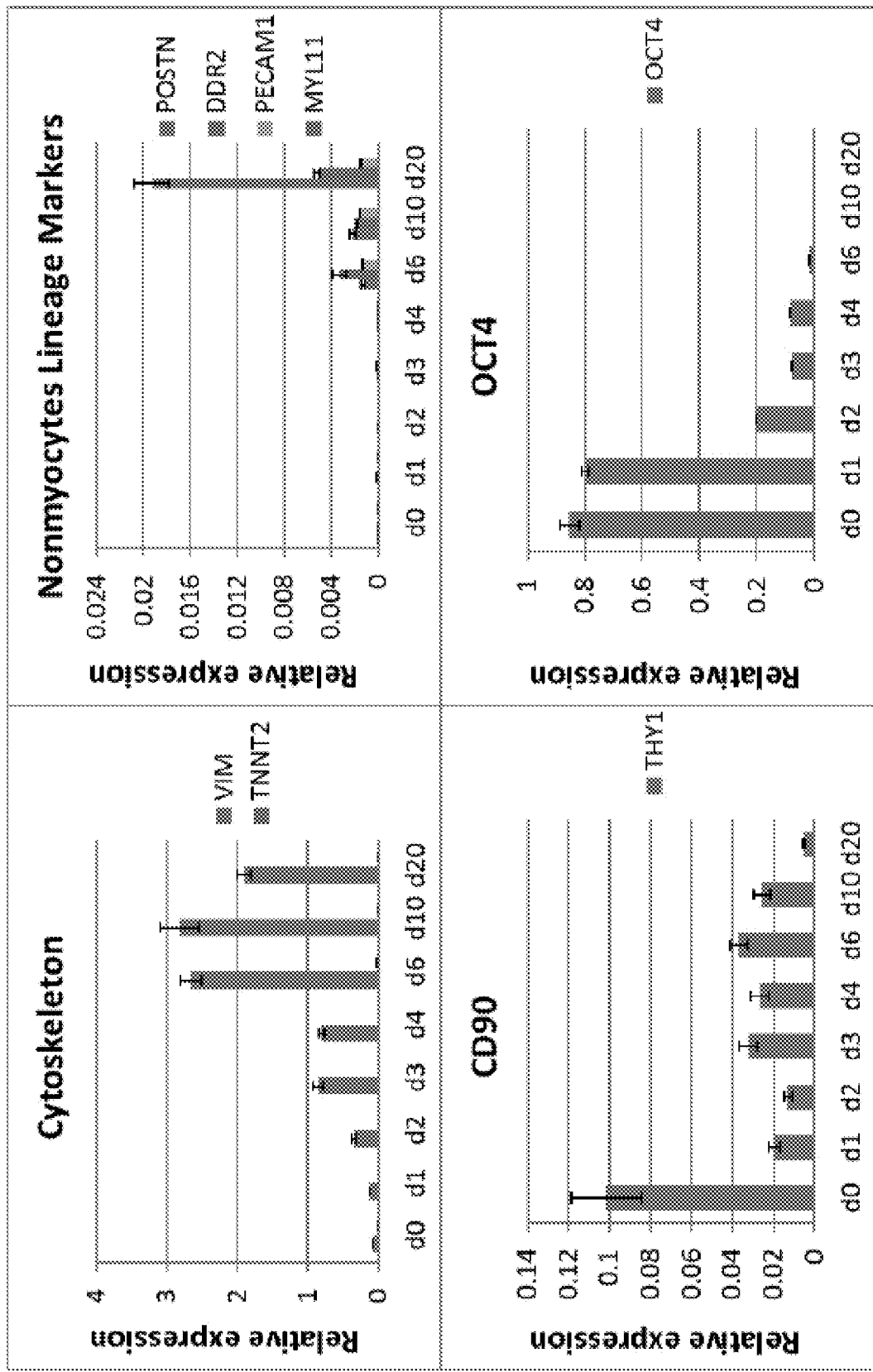

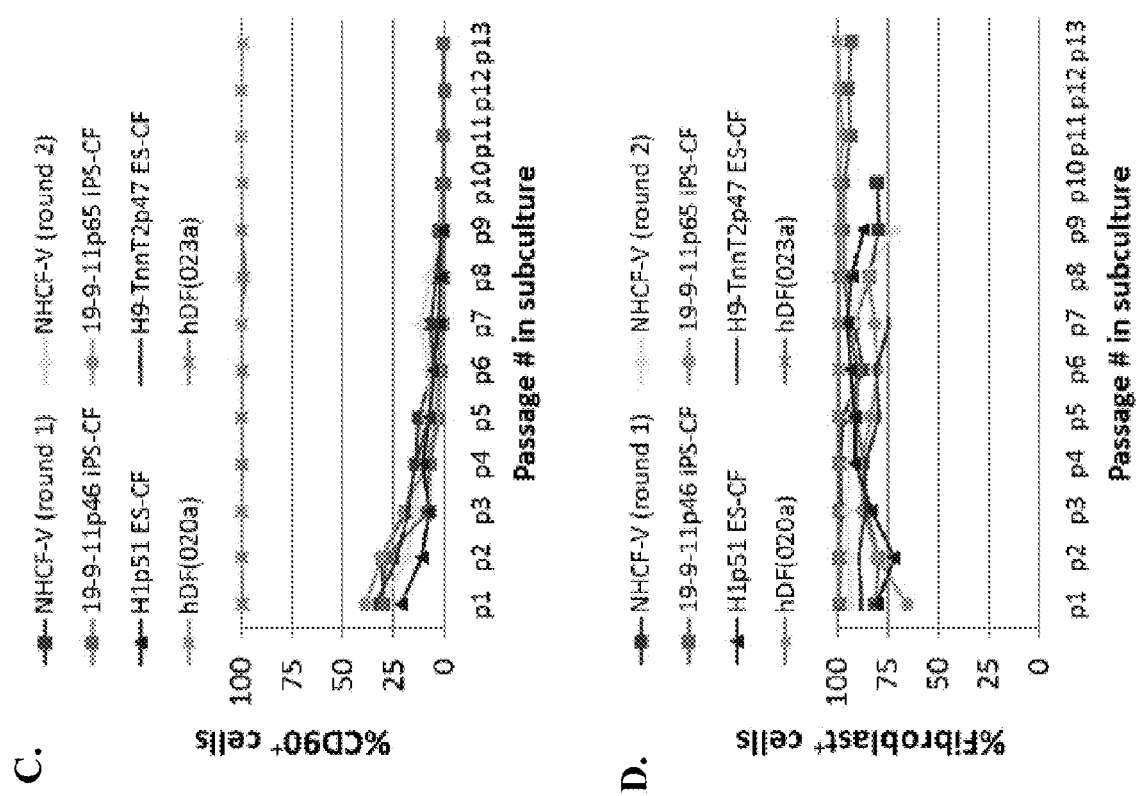
FIGS. 3A-3G, CONTINUED

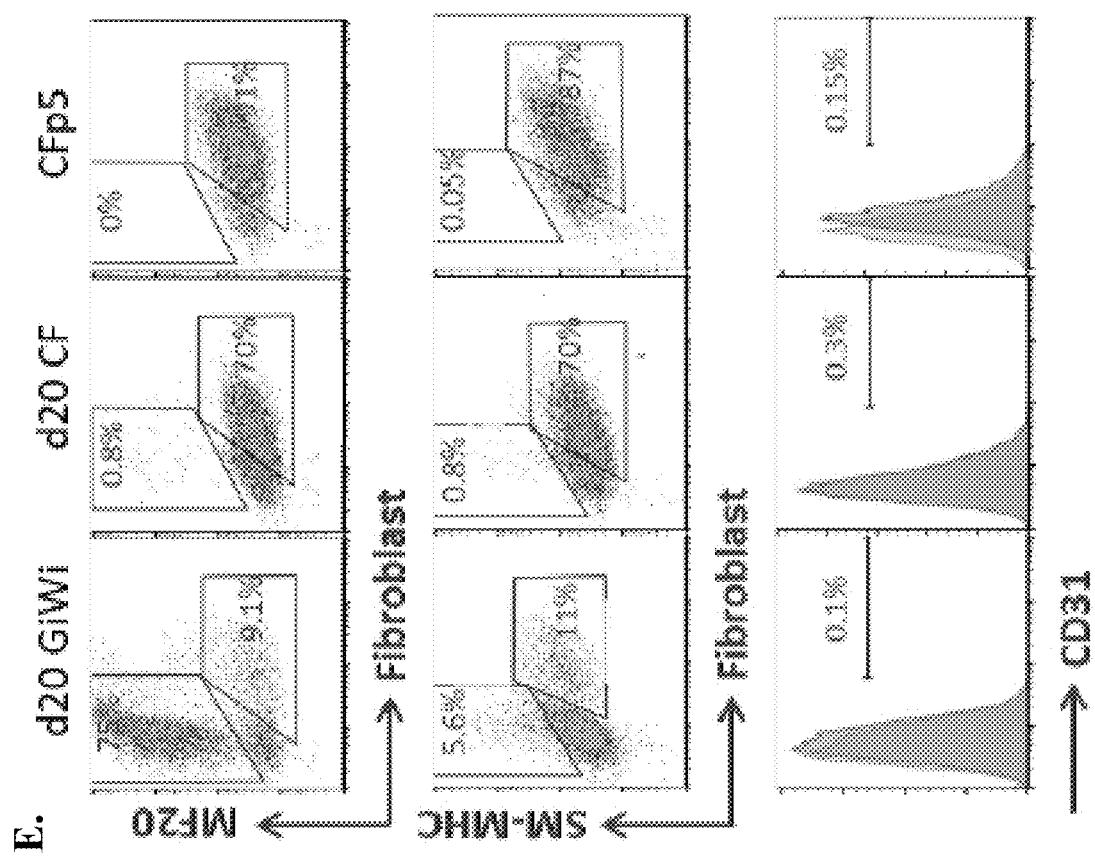
FIGS. 3A-3G, CONTINUED

FIGS. 3A-3G, CONTINUED
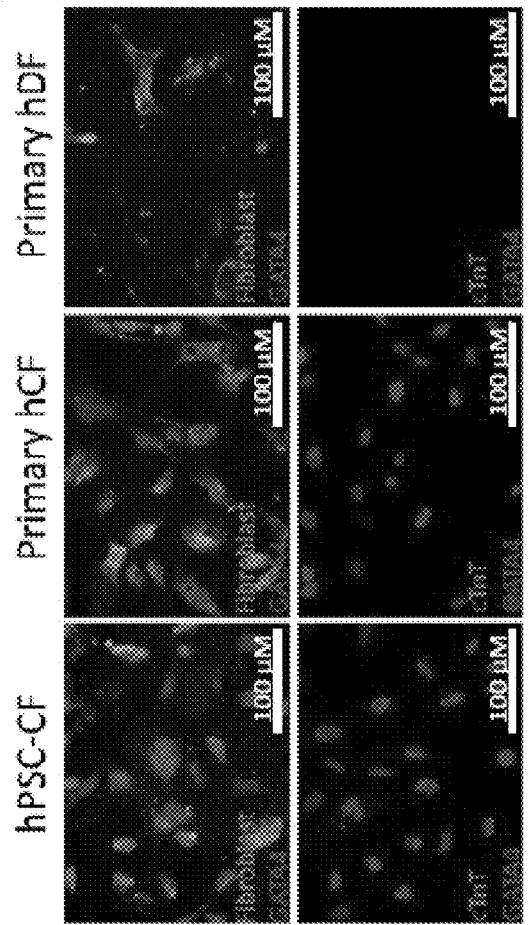
F.
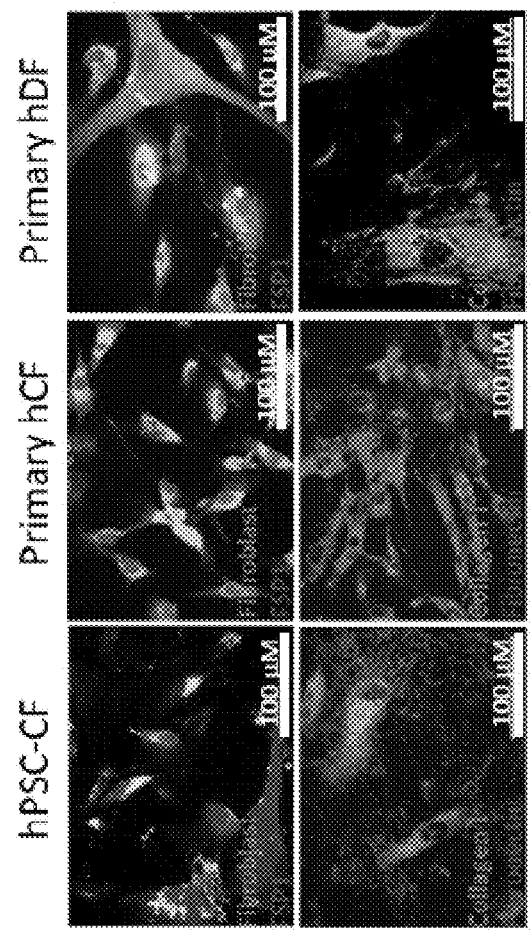
G.

A.

FIGS. 4A-4F, CONTINUED
Cardiac Factors
B.
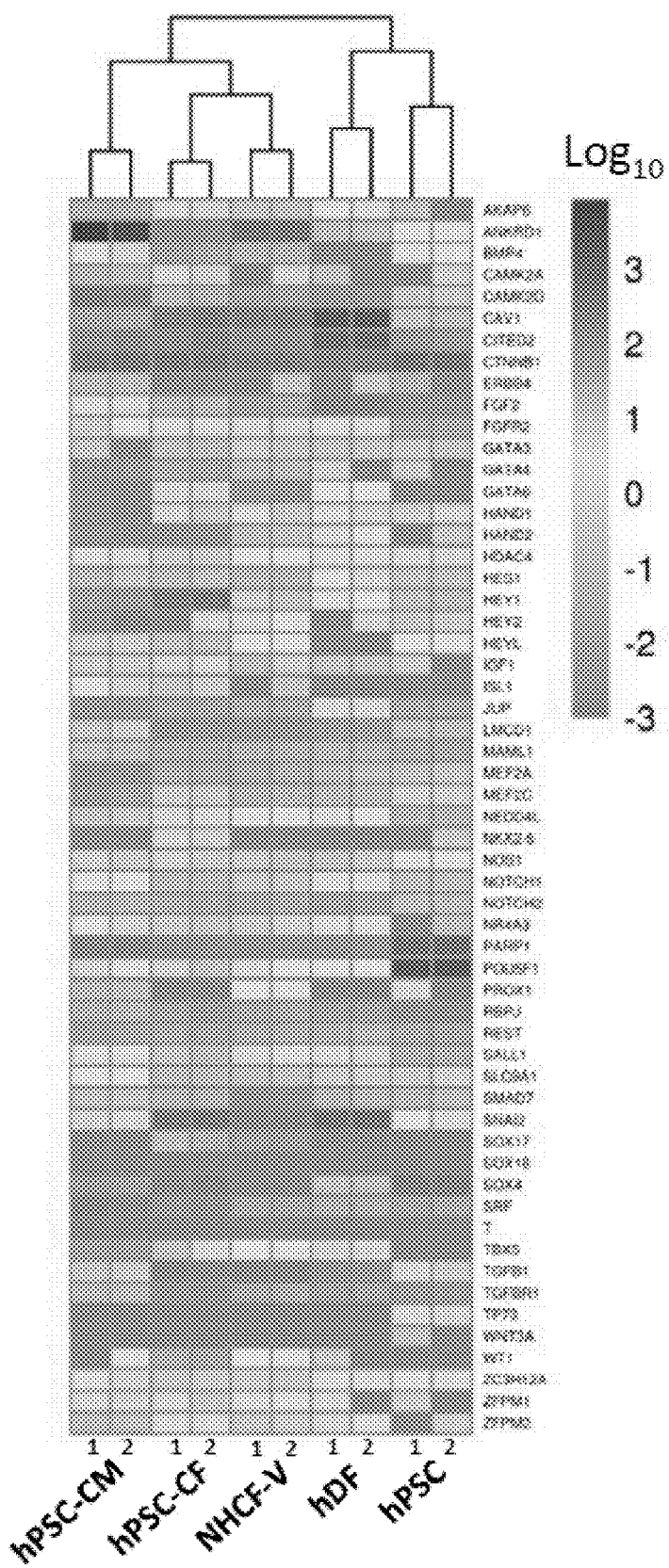

FIGS. 4A-4F, CONTINUED
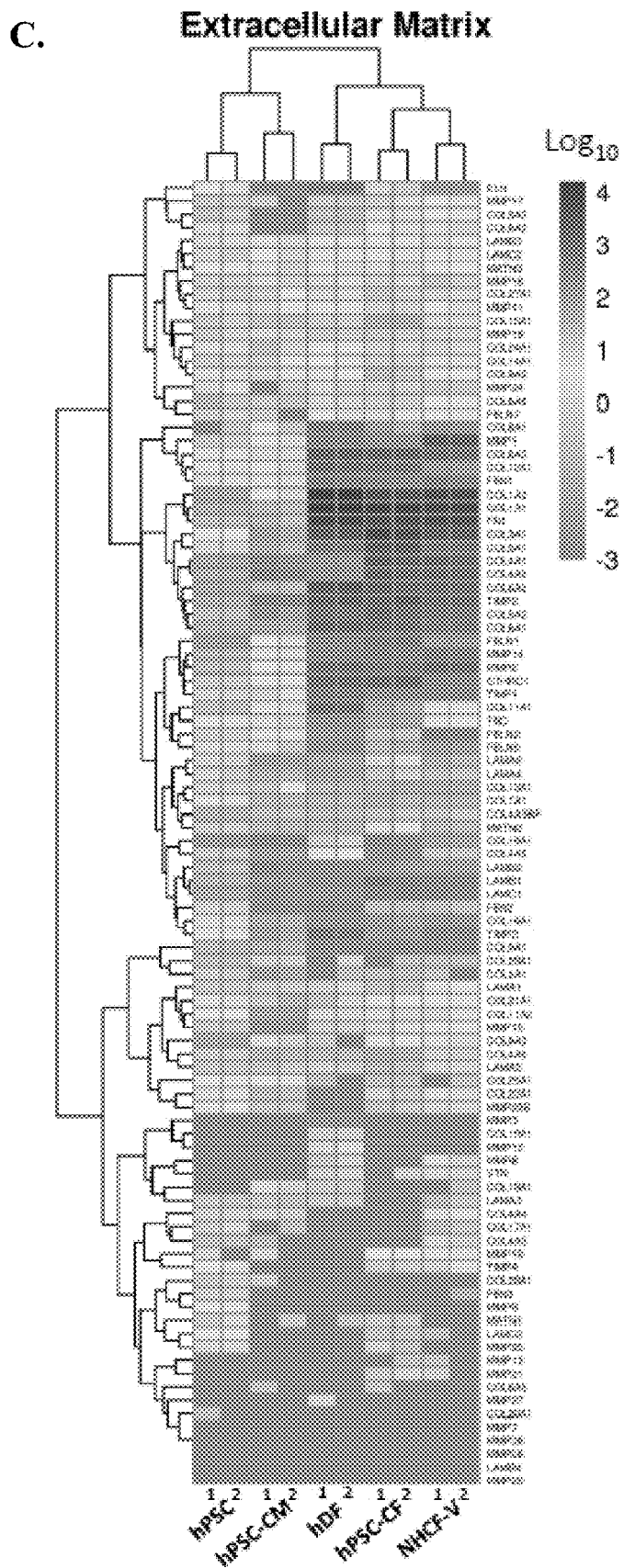

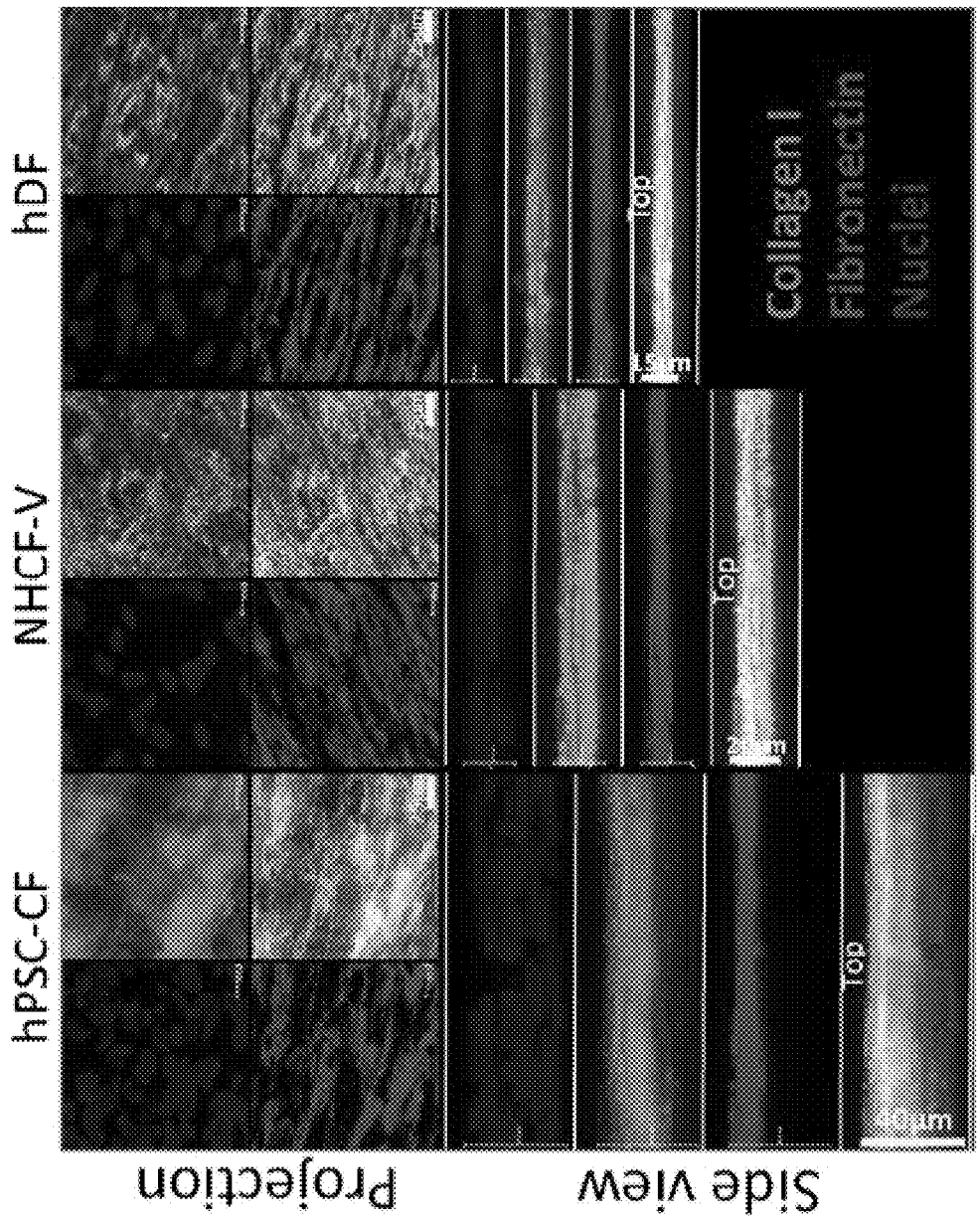
FIGS. 4A-4F, CONTINUED

FIGS. 4A-4F, CONTINUED
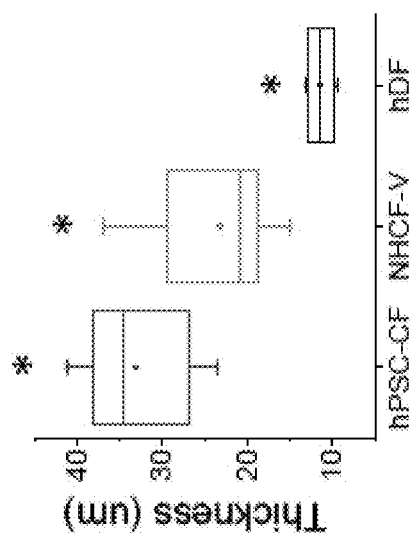
E.

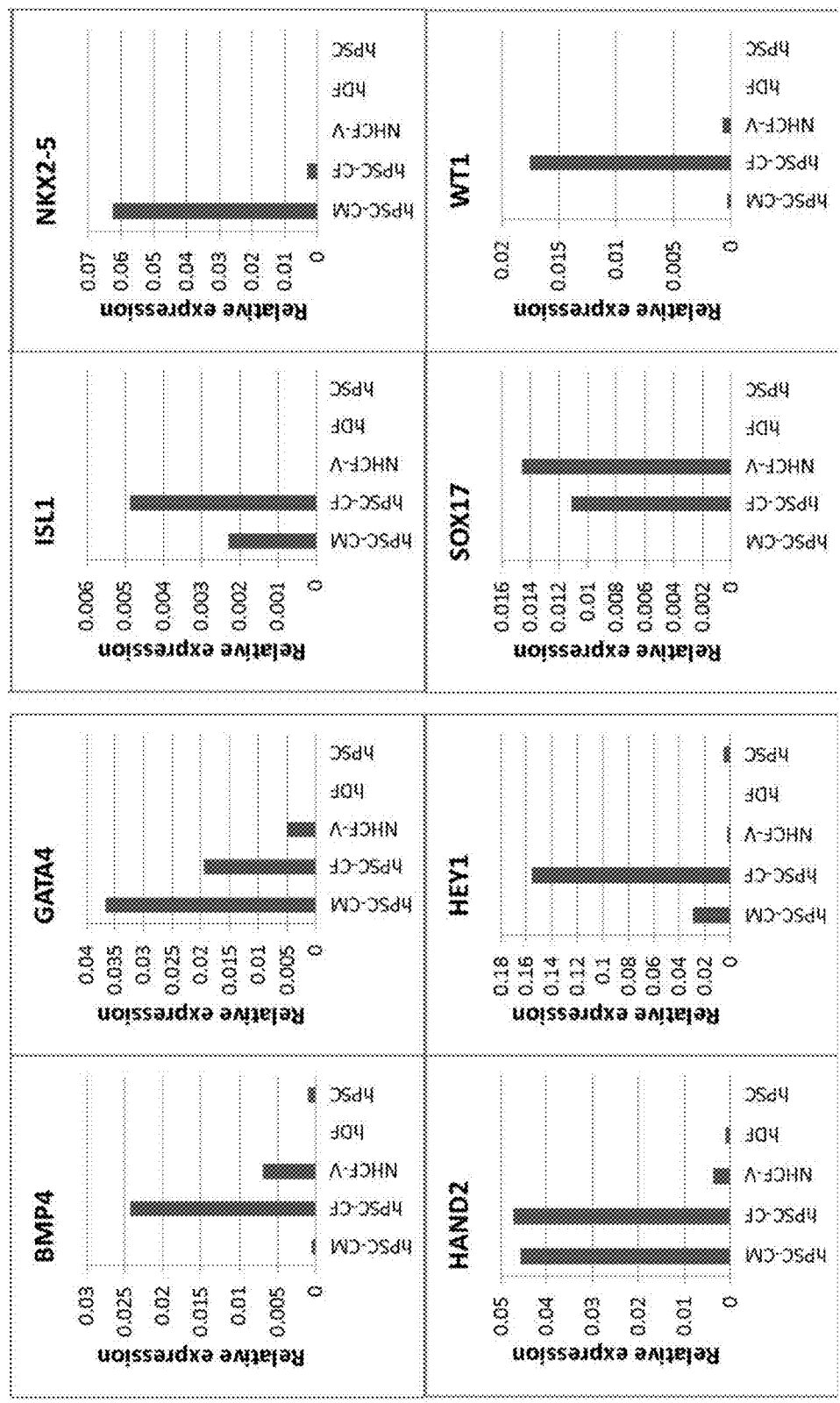
FIGS. 4A-4F, CONTINUED

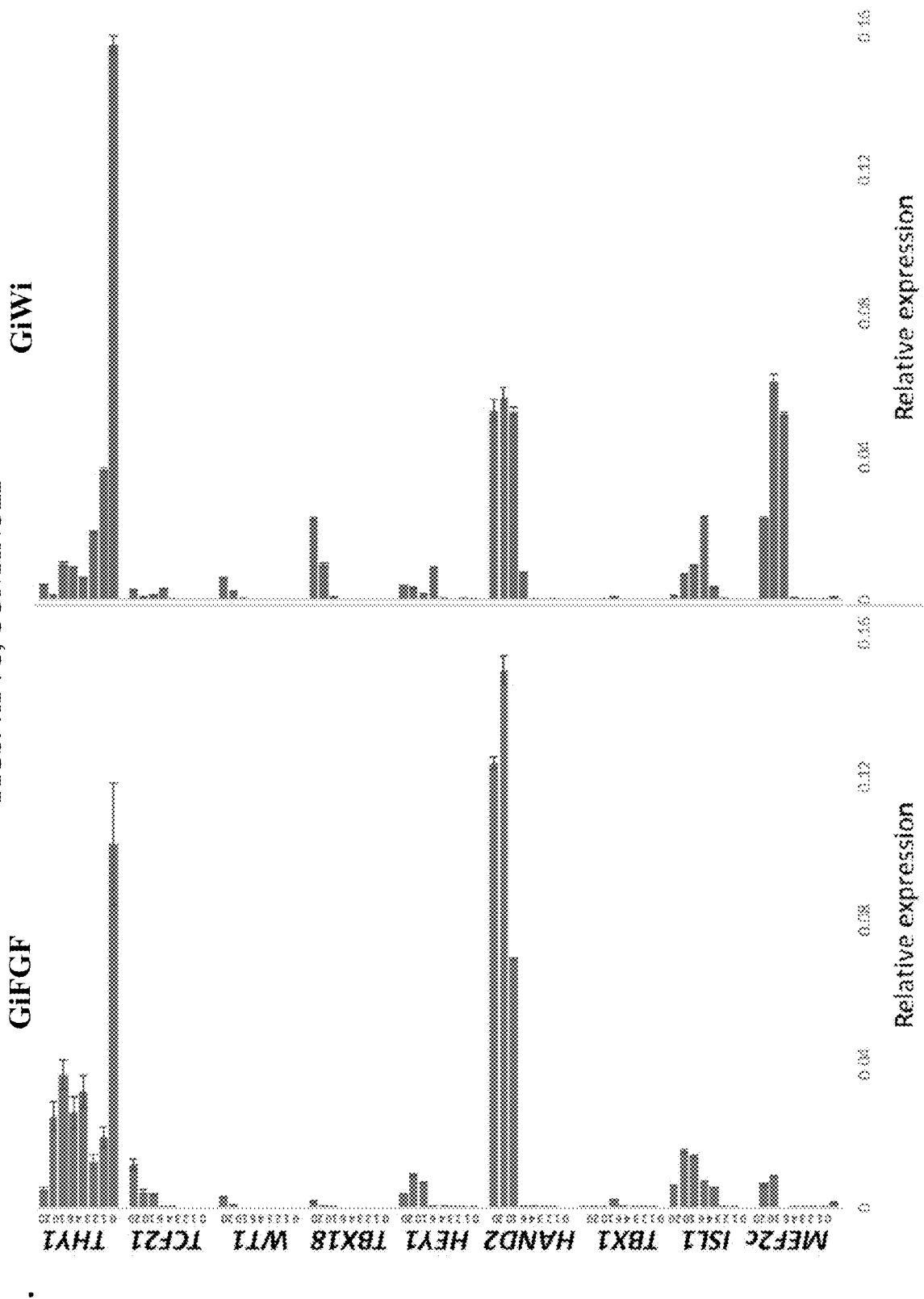
FIGS. 7A-7C, CONTINUED

FIGS. 7A-7C, CONTINUED
B, CONTINUED.
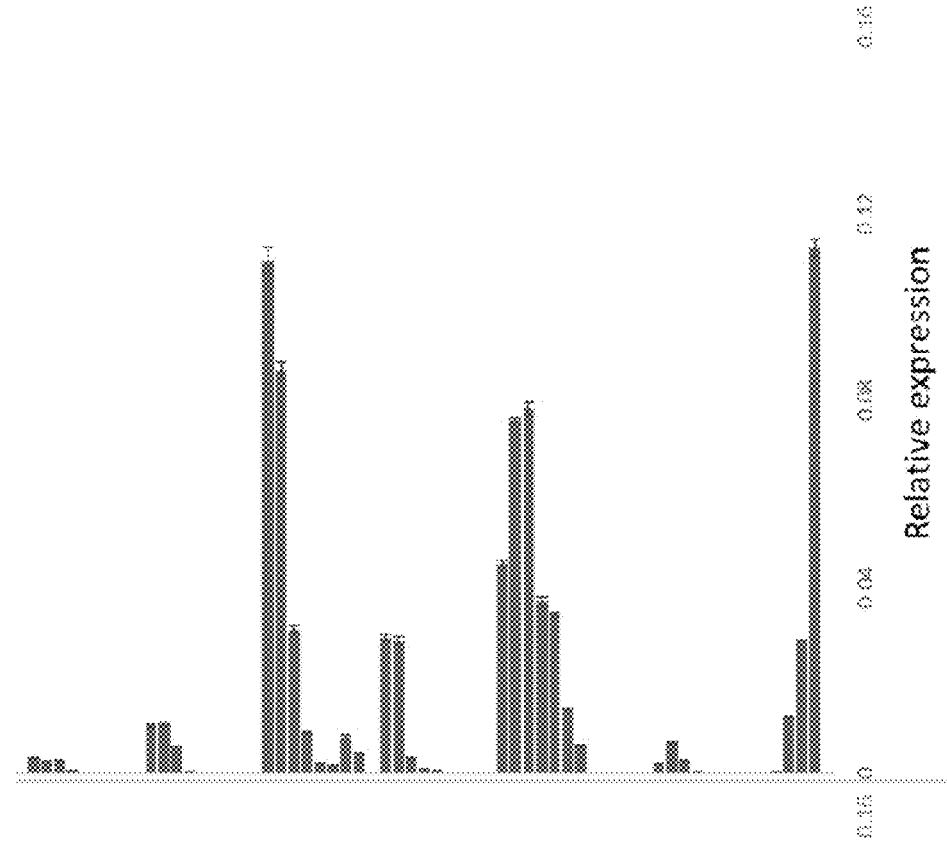

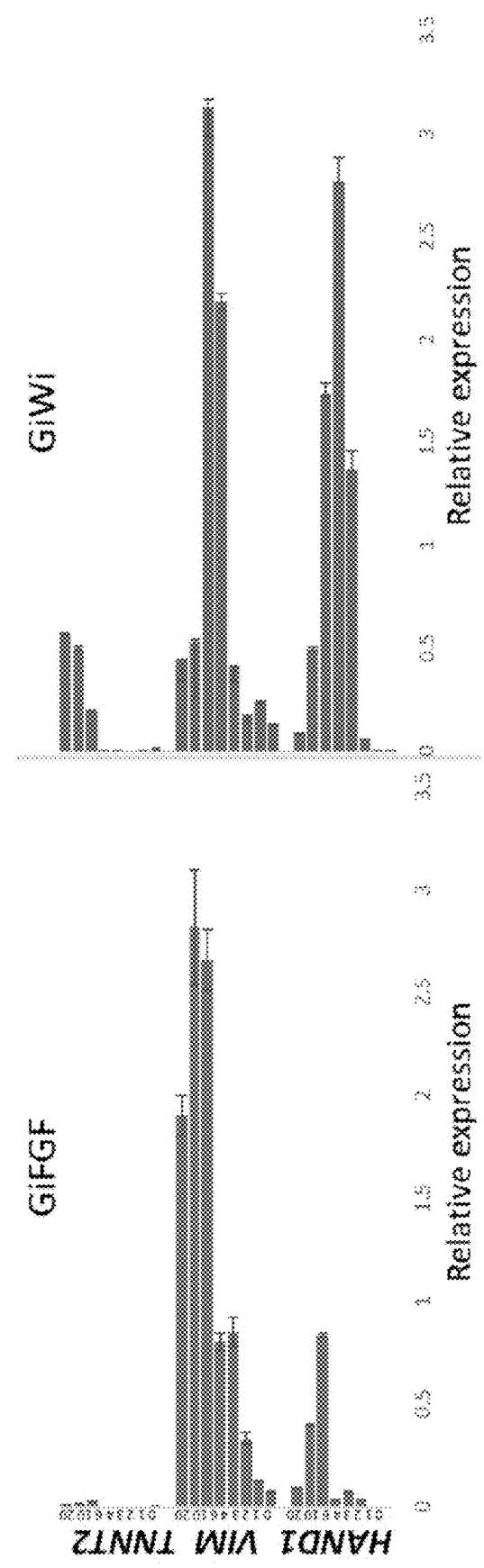
FIGS. 7A-7C, CONTINUED

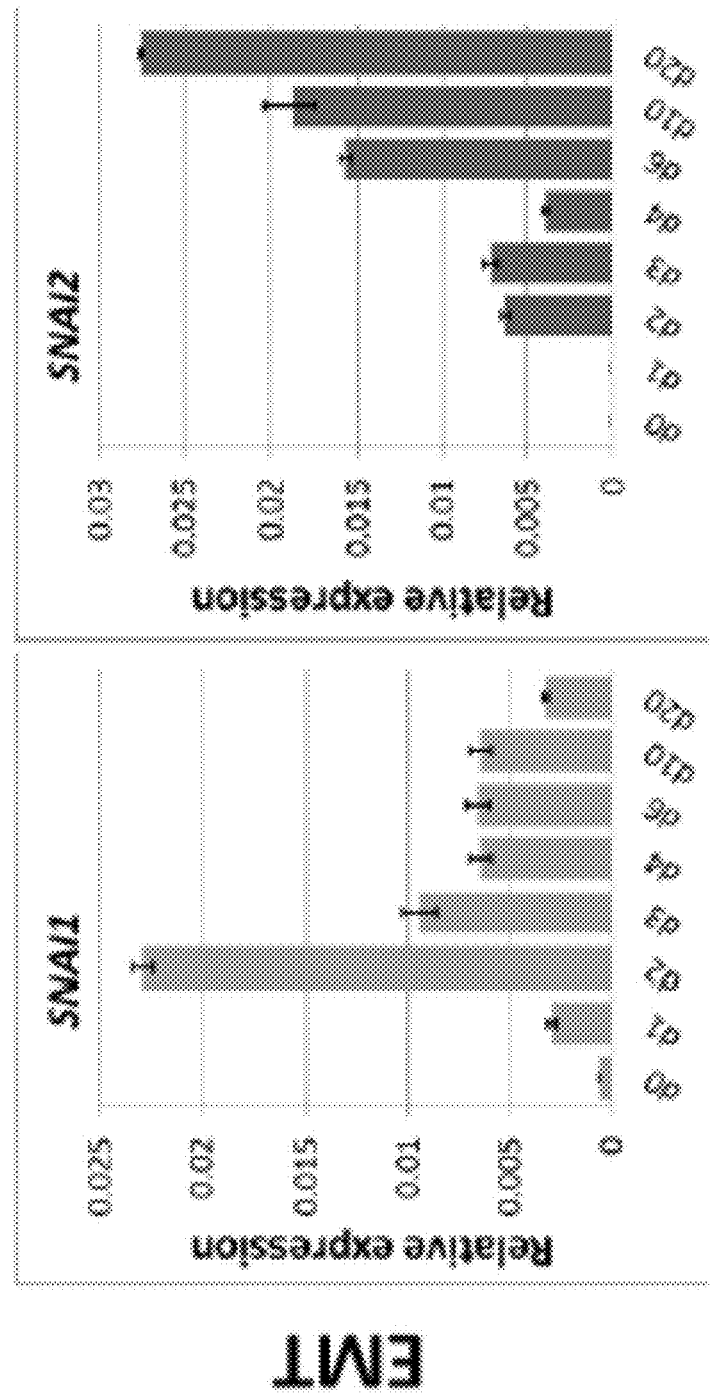
FIGS. 7A-7C, CONTINUED

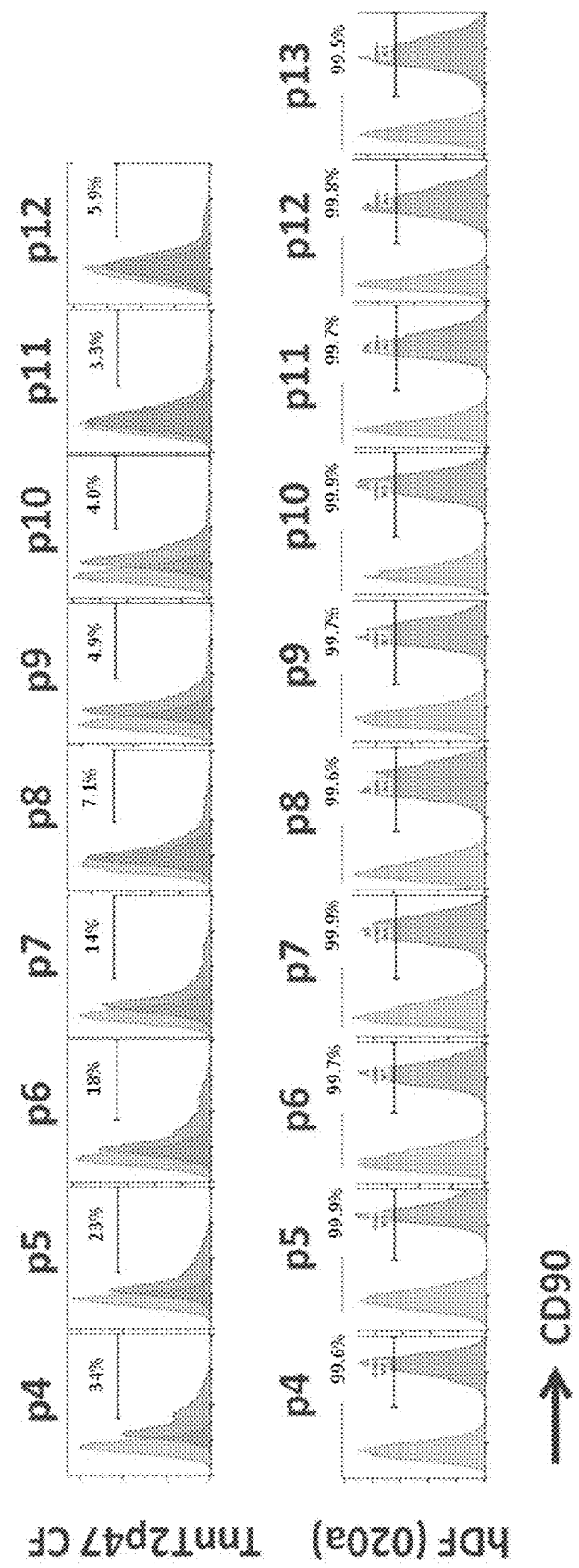
FIG. 8, CONTINUED

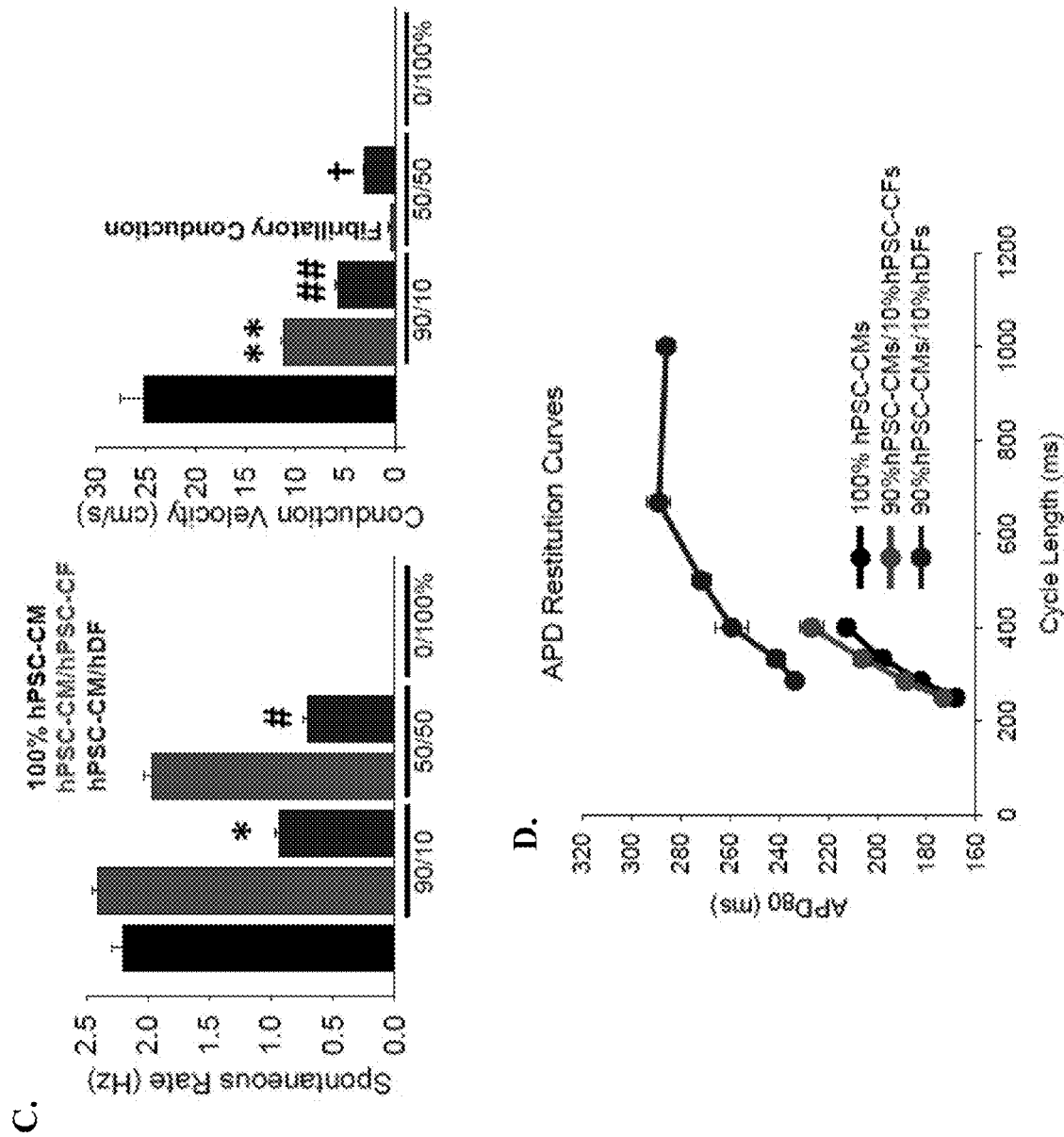
FIGS. 10A-10D, CONTINUED

METHOD OF DIFFERENTIATING HUMAN PLURIPOTENT CELLS INTO CARDIAC FIBROBLASTS

CROSS-REFERENCE TO RELATED APPLICATIONS

This application claims the benefit of U.S. Provisional Patent Application No. 62/402,694, filed Sep. 30, 2016, which is incorporated by reference in its entirety.

STATEMENT REGARDING FEDERALLY SPONSORED RESEARCH OR DEVELOPMENT

This invention was made with government support under HL099773 and HL129798 awarded by the National Institutes of Health. The government has certain rights in the invention.

BACKGROUND

The heart is comprised of multiple types of cells including cardiomyocytes, fibroblasts, endothelial cells, and vascular smooth muscle cells. Although cardiomyocytes occupy about 70% of the heart by volume, by cell number, non-myocytes are the majority of cells in the myocardium (Vliegen et al., *European Heart* 1, 1991). Non-myocytes include cardiac fibroblasts (CFs), endothelial cells, and smooth muscle cells as well as circulating cells present in the heart. Previous studies have shown that CFs constitute either the most common or second most common non-myocyte cell type in mammalian hearts depending on the methodology used and species studied (Anversa et al., *J. Molecular Cell. Cardiology* 12(8):781-795, 1980; Nag, *Tissue & Cell* 12(1):125-139, 1980; Banerjee et al., *Am. J. Physiol.—Heart and Circulatory Physiology* 293(3):H1883-H1891, 2007; Bergmann et al., *Cell* 161(7):1566-1575, 2015; Pinto et al., *Circ. Res.* 118(3) 2016).

Early activation of the cardiomyogenic transcriptional program in anterior lateral splanchnic mesoderm is mediated by positive and negative signals from adjacent endoderm, overlying ectoderm, and midline structures, including bone morphogenetic protein (BMP), fibroblast growth factor (FGF), and canonical and noncanonical Wnt signaling (Evans et al., 2010). As the cardiac crescent and linear heart tube form, second heart field (SHF) cells in medial splanchnic mesoderm remain in contact with pharyngeal endoderm and their continued proliferation and delayed differentiation is regulated by canonical Wnt, FGF, and Hedgehog (Hh) signaling pathways (Kelly R G, *Curr Topics Dev Biol* 100:33-65, 2012). The roles of these signaling pathways have been dissected using experimental manipulation in avian embryos and conditional mutagenesis in the mouse, which show that Wnt/β-catenin signaling plays an upstream role in promoting proliferation of SHF cells in vivo, and FGF ligands expression is downstream of canonical Wnt signaling (Cohen et al., 2007; Lin et al., 2007). FGF8 is thought to be the major FGF ligand driving SHF proliferation in vivo, with important contributions from FGF10 and FGF3 as revealed by analysis of compound mutant embryos (Ilagan et al., 2006; Park et al., 2006, 2008; Urness et al., 2011; Watanabe et al., 2010).

Although the CFs are not as well studied as cardiomyocytes, investigations over the last two decades have demonstrated multiple important roles of CFs in cardiac development, homeostasis, and response to injury (Lajiness & Conway, 2012). CFs are best known for generating the extracellular matrix that helps form the heart and regulate its function. For example, CFs are known to secrete collagen I and III abundantly as well as fibronectin and various proteoglycans. A second major function of CFs is the secretion of cytokines and growth factors. During development, signaling from CFs is necessary to stimulate myocyte growth and cell division as well as to dynamically remodel the extracellular matrix (Ieda et al., 2009). CFs play a central role in many forms of heart disease. In cardiac hypertrophy, which is the most significant risk factor for cardiac events and cardiac death, CFs contribute abnormal matrix synthesis. CFs also are intimately involved in many of the well-known signaling pathways linked to heart disease. For example, β-adrenergic receptors are present on CFs, and the beneficial impact of β-adrenergic blockers in disease states such as heart failure likely are in part due to effects on CFs (D'Souza et al., 2011). Following a myocardial infarction or other form of inflammation or stress impacting the myocardium, CFs can become activated, generating myofibroblasts which produce the pathological fibrosis which is a major contributor to organ dysfunction. Increased numbers of cardiac fibroblasts and fibrosis also lead to abnormal electrical conduction and increased risks for arrhythmias and sudden cardiac death (Kohl & Gourdie, 2014). Furthermore, while fibroblasts have been regarded as a common mesenchymal cell present in most tissues, distinct gene expression patterns and characteristics are beginning to define tissue-specific fibroblasts. For example, CFs have been demonstrated to express cardiac-specific genes highlighted by the expression of the transcription factors GATA4 and Tbx20 (Furtado et al., 2014).

Human CFs hold promise for a variety of applications. Although cardiac cell therapy is actively being investigated by many groups around the world, clinically tested cell preparations have proven disappointing. CFs can be obtained from animal hearts for research, but human-specific biology is most accurately reflected by human CFs. Primary, viable human CFs are difficult to obtain from human cardiac samples obtained by heart biopsies, cardiac surgery, or at autopsy. In addition, primary CFs can be passaged only a limited number of times before senescence. Thus a robust and reliable source of human CFs is needed for cardiovascular research and therapeutic applications. Accordingly, there is a need in the art for efficient and cost-effective protocols for generating functional cardiac fibroblasts under chemically defined culture conditions and in the absence of certain growth factors previously thought to be an essential part of directed cardiac fibroblast differentiation.

BRIEF SUMMARY

The invention relates generally to methods for generating functional cardiac fibroblasts from hPSCs populations under chemically-defined conditions and for long-term maintenance of such hPSC-derived cardiac fibroblast cell populations.

In a first aspect, provided herein is a method for generating a population of cardiac fibroblast cells, the method comprising: culturing human cardiac mesoderm progenitor cells in a chemically defined culture medium comprising a fibroblast growth factor, whereby a cell population comprising human cardiac fibroblast cells is obtained after about 20 days in culture. The fibroblast growth factor can be bFGF/FGF2. At least 90% of cells in the cell population can be cardiac fibroblast cells positive for expression of one or more markers selected from the group consisting of GATA4, HAND2, HEY1, ISL1, NKX2-5, SOX17, BMP4, and WT1. In some cases, no cell separation or selection step is used to obtain the cell population comprising cardiac fibroblasts. The cardiac fibroblast cells can be capable of undergoing at least 10 cell divisions. The human cardiac mesoderm progenitor cells can be obtained from a method comprising culturing human pluripotent stem cells cultured in a chemically defined culture medium comprising an activator of Wnt/β-catenin signaling for about 2 to about 3 days, whereby a cell population comprising cardiac mesodermal cells positive for expression of Brachyury/T. The activator of Wnt/β-catenin signaling can be a Gsk3 inhibitor. The Gsk3 inhibitor can be a small molecule selected from the group consisting of CHIR99021, CHIR98014, BIO-acetoxime, BIO, LiCl, SB216763, SB415286, AR A014418, 1-Azakenpaullone, and Bis-7-indolylmaleimide. The Gsk3 inhibitor can be CHIR99021 present in a concentration of about 0.2 μM to about 20 μM. The Gsk3 inhibitor can be CHIR99021 present in a concentration of about 12 μM.

In a second aspect, provided herein is a method for generating a human arrhythmia model, the method comprising the steps of: co-culturing a population of cardiac fibroblast cells in the presence of a population of cardiomyocytes in a chemically defined culture medium. The cardiac fibroblast cells can be generated by a method comprising culturing human cardiac mesoderm progenitor cells in a chemically defined culture medium comprising a fibroblast growth factor, whereby a cell population comprising human cardiac fibroblast cells is obtained after about 20 days in culture. The co-culture can include 10%, 50%, 70%, or 90% cardiac fibroblast cells. The co-culture can be seeded at a density between about 60,000 cells/cm2 and about 120,000 cells/cm2.

In a third aspect, provided herein is a method of screening a test agent, the method comprising: co-culturing a population of cardiac fibroblast cells in the presence of a population of cardiomyocytes in a chemically defined culture medium; contacting the co-culture with a test agent; measuring a functional parameter of the contacted co-culture; and comparing the functional parameter to that parameter measured in a co-culture which has not been contacted with the test agent, wherein modulation of the functional parameter after contact with the test agent indicates the test agent is a candidate therapeutic agent. The test agent can be selected from the group consisting of (i) an organic compound; (ii) a nucleic acid; (iii) a peptide; (iii) a polypeptide; and (iv) an antibody. The functional parameter can be selected from the group consisting of electrical impulse propagation pattern, conduction velocity, and action potential duration. The electrical impulse propagation pattern can be measured using a fluorescent membrane potential dye. Acceleration of the conduction velocity after contact with the test agent can indicate the test agent is a candidate therapeutic agent. Prolongation of the action potential duration after contact with the test agent can indicate the test agent is a candidate therapeutic agent. The electrical impulse propagation pattern can be measured as the fibrillatory or reentry pattern and an increase in the pattern after contact with the test agent indicates the test agent is a candidate therapeutic agent. The cardiac fibroblast cells can be generated by a method comprising culturing human cardiac mesoderm progenitor cells in a chemically defined culture medium comprising a fibroblast growth factor, whereby a cell population comprising human cardiac fibroblast cells is obtained after about 20 days in culture.

In a fourth aspect, provided herein is a chemically defined culture medium comprising: a fibroblast growth factor, glutamine, ascorbic acid, hydrocortisone hemisuccinate, insulin, and DMEM. The glutamine can be provided as GlutaMAX. The medium can additionally comprise human serum albumin, linoleic acid, and lecithin. The medium is xeno-free.

In a fifth aspect, provided herein is a kit for differentiating human pluripotent stem cells into cardiac fibroblasts, the kit comprising: (i) a chemically defined culture medium suitable for differentiating human cardiac progenitor cells into cardiac fibroblasts; (ii) an agent that activates Wnt signaling in human cardiac progenitor cells; (iii) a fibroblast growth factor; and (iv) instructions describing a method for generating human CFs, the method employing the culture medium, the agent, and the fibroblast growth factor. The chemically defined culture medium of (i) can comprise a fibroblast growth factor, GlutaMAX, ascorbic acid, hydrocortisone hemisuccinate, insulin, and DMEM. The agent that actives Wnt signaling can be a Gsk3 inhibitor. The Gsk3 inhibitor can be a small molecule selected from the group consisting of CHIR99021, CHIR98014, BIO-acetoxime, BIO, LiCl, SB216763, SB415286, AR A014418, 1-Azakenpaullone, and Bis-7-indolylmaleimide.

These and other features, objects, and advantages of the present invention will become better understood from the description that follows. In the description, reference is made to the accompanying drawings, which form a part hereof and in which there is shown by way of illustration, not limitation, embodiments of the invention. The description of preferred embodiments is not intended to limit the invention to cover all modifications, equivalents and alternatives. Reference should therefore be made to the claims recited herein for interpreting the scope of the invention.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The present invention will be better understood and features, aspects and advantages other than those set forth above will become apparent when consideration is given to the following detailed description thereof. Such detailed description makes reference to the following drawings, wherein:

(FIG. 1A) Schematic method of the cardiomyocyte differentiation protocol ("GiWi protocol") and markers for stage-specific progenitors. (FIG. 1B) Flow cytometric analysis of stage-specific progenitors generated in early differentiation (day 0-5) in the GiWi protocol from iPSC line 19-9-11. (FIG. 1C) Schematic method for cardiac fibroblast differentiation induced by bFGF at the stage-specific progenitors. (FIG. 1D) Flow cytometric analysis demonstrates changes in the abundance of cardiac fibroblast populations based on timing of bFGF/FGF2 exposure and dose. (FIG. 1E) Average percentage of fibroblast population differentiated from hPSC lines at 20 days. CFBM, cardiac fibroblast basal medium (Table 1); MF20, antibody for sarcomere myosin (Table 2); Fibroblast, antibody for fibroblast (Table 2). (FIG. 1F) Stage-specific progenitors induced by bFGF signaling in cardiac fibroblast differentiation (red).

(FIG. 2A) Schematic method of the GiFGF protocol and stage-specific progenitors in differentiation of hPSCs to cardiac fibroblasts. (FIG. 2B) qRT-PCR showing the transcription factors expression and hierarchy in the time course of the GiFGF protocol (day 0-20). (FIG. 2C) qRT-PCR showing expression of markers for fibroblasts, cardiomyocytes and nonmyocyte lineages in the time course of the GiFGF protocol (day 0-20). MP, mesodermal progenitor; CMP, cardiac mesodermal progenitor; SHFP, second heart field progenitor; CF, cardiac fibroblast.

(FIG. 3A) Morphology of hPSC-CF (iPSC line DF19-9-11T derived CF), primary cardiac fibroblast (NHCF-V) and human dermal fibroblast (hDF). (FIG. 3B) Growth capacity of hPSC-CF and NHCF-V during passaging. (FIG. 3C) CD90 expression by flow cytometry in hPSC-CF, NHCF-V and hDF during passaging. (FIG. 3D) The fibroblast marker (clone TE-7) expression by flow cytometry in hPSC-CF, NHCF-V and hDF during passaging. (FIG. 3E) Markers expression for endothelial cells (CD31), smooth muscle cells (SM-MHC) and cardiomyocytes (MF20) examined by flow cytometry in the 20 day hPSC-differentiated CMs by GiWi protocol, and CFs by GiFGF protocol and the CFs at passage 5. (FIGS. 3F-3G) Immunolabeling by antibodies for fibroblast (clone TE-7), cTnT, Gata4 (FIG. 3F), and fsp1, collagen I and fibronectin (FIG. 3G) in hPSC-CF, NHCF-V and hDF showing Gata4 only expressed in cardiac fibroblasts, not in dermal fibroblasts, while fibroblast, fsp1, collagen I and fibronectin expressed in all fibroblasts.

(FIG. 4A) Dendrogram of similarity in the abundance of overall transcripts (19,084 genes) across samples of hPSC-CFs, NHCF-V, hDF, hPSC-CM and hPSC and calculated by Euclidean distance. (FIG. 4B) Heatmap of cardiac factors (57 genes) expression across samples of hPSC-CFs, NHCF-V, hDF, hPSC and hPSC-CM. (FIG. 4C) Heatmap of extracellular matrix related gene expression (98 genes) across samples of hPSC-CFs, NHCF-V, hDF, hPSC and hPSC-CM. (FIG. 4D) Confocal z-scan images of collagen I and fibronectin immunolabeling showing the 3D reconstruction of collagen and fibronectin extracellular matrix relative to the cells in the high density culture of hPSC-CF, NHCF-V and hDF. (FIG. 4E) Thickness of the 3D ECM scaffolds of hPSC-CF, NHCF-V and hDF. *$P<0.05$, one-way ANOVA with post-hoc tests. (FIG. 4F) Relative expression of cardiac factors BMP4, GATA4, HAND2, HEY1, ISL1, NKX2-5, SOX17 and WT1 (fold change normalized to GAPDH) in hPSC-CFs, NHCF-V, hDF, hPSC, and hPSC-CM.

(FIG. 7A) FHF and SHF specific gene expression in the GiFGF and GiWi protocols. (FIG. 7B) Gene expression pattern in GiFGF and GiWi protocols (day 0-20). (FIG. 7C) Relative gene expression (normalized to GAPDH) by quantitative RT-PCR of transcription factors of EMT (Epithelial to Mesenchymal Transition) in the time course of cardiac fibroblast differentiation using the GiFGF protocol.

(FIG. 10A) confocal images showing the ratios of hPSC-CMs co-cultured with hPSC-CFs for use in functional experiments. (FIG. 10B) Time-space plots of optical mapping experiments. Post acquisition analysis of optical recordings was done by plotting the changes of fluorescence over time over a single line of each monolayer-similar to a confocal line scan. Each spontaneous activation is represented by a flash of light which propagated over the entire monolayer shown in these 5s recordings. (FIG. 10C) Quantification of spontaneous beating rate (Hz) and action potential propagation velocity (cm/s). Beating rate of 100% CM monolayers was 2.2±0.09 Hz. 10% hPSC-CFs increased beating rate frequency to 2.4±0.05 Hz; 50% hPSC-CFs resulted in average beating rate of 1.9±0.06 Hz. hPSC-CFs did not significantly change the spontaneous beating rate of these monolayers. On the other hand, 10% hDF significantly reduced the beating rate to 0.93±0.03 Hz (*$P=2.6\times10-7$) and 50% hDF reduced the beating rate to 0.7±0.04 Hz (#$P=7.0\times10-8$); unpaired t-test each compared to 100% CM monolayers. Conduction velocity of 100% CM monolayers was 25.2±2.4 cm/s. 10% hPSC-CFs reduced velocity to 11.1±0.34 cm/s and hDFs reduced conduction velocity to a greater extent, to 5.7±0.27 cm/s. 50% hPSC-CFs caused fibrillatory conduction which precluded quantification of impulse propagation velocity and 50% hDFs further reduced conduction velocity to 2.6±0.14 cm/s. Comparisons with 100% CM monolayers: **$P=1.1\times10^{-4}$; ##$P=7.9\times10^{-6}$; †$P=2.5\times10^{-6}$; unpaired t-tests. (FIG. 10D) APD80 restitution curves show that hDFs have distinct effect on cardiac monolayer compared to hPSC-CFs. Data shown for 10% hDF or hPSC-CF co-culture condition.

Figures 1A, 1B, 1C, 1D, 1E, 1F:
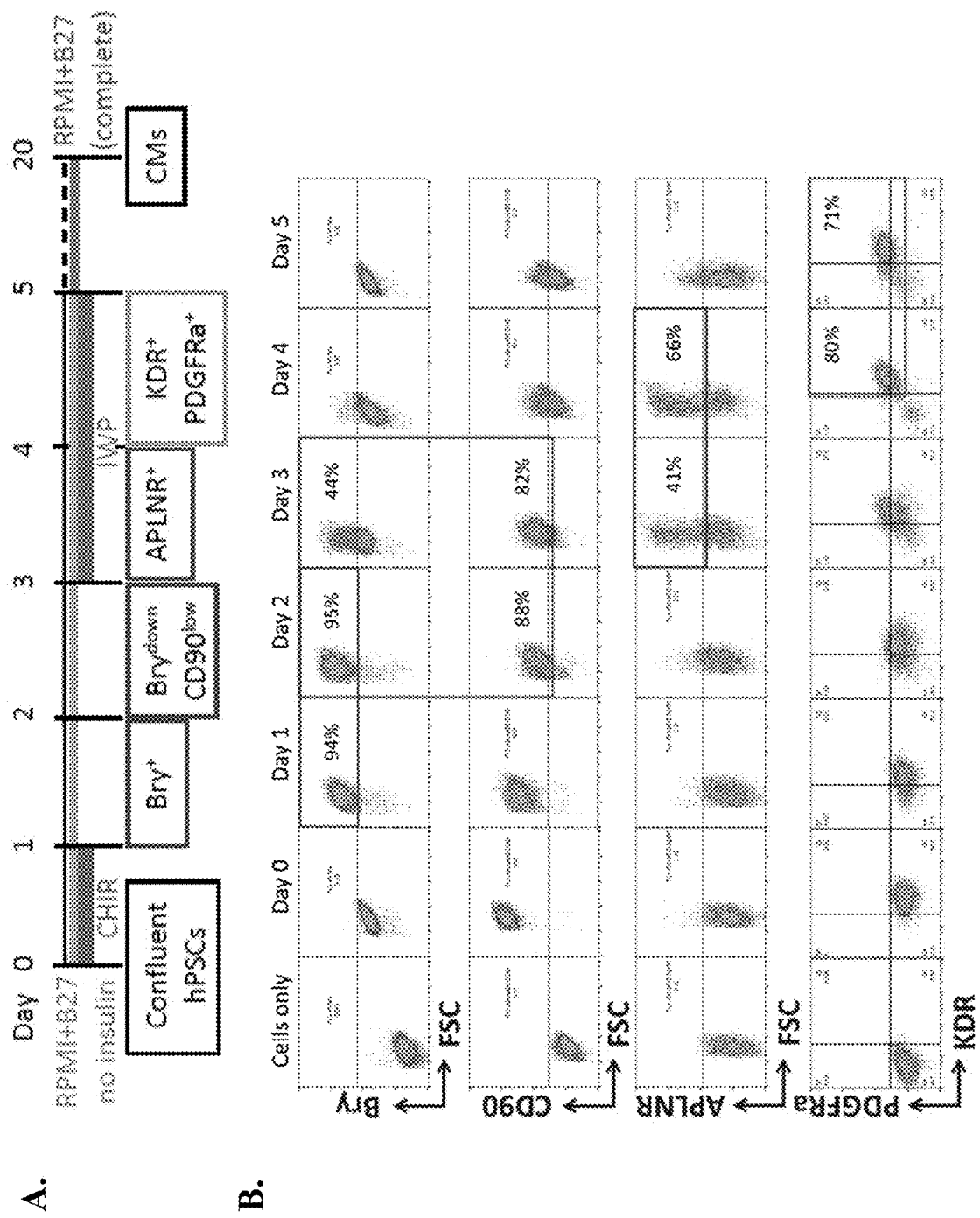
FIGS. 1A-1F demonstrate derivation of cardiac fibroblasts from stage-specific progenitors from human pluripotent stem cells (hPSCs).

While the present invention is susceptible to various modifications and alternative forms, exemplary embodiments thereof are shown by way of example in the drawings and are herein described in detail. It should be understood, however, that the description of exemplary embodiments is not intended to limit the invention to the particular forms disclosed, but on the contrary, the intention is to cover all modifications, equivalents and alternatives falling within the spirit and scope of the invention as defined by the appended claims.

DETAILED DESCRIPTION

All publications, including but not limited to patents and patent applications, cited in this specification are herein incorporated by reference as though set forth in their entirety in the present application.

The methods and compositions provided herein are based at least in part on the Inventors' discovery that differentiation stage-specific modulation of canonical Wnt signaling and FGF signaling is sufficient to efficiently obtain cardiac fibroblasts from human pluripotent stem cells (hPSCs) under chemically defined conditions. Activation of Wnt signaling induces mesodermal differentiation, while subsequent Wnt inhibition drives cardiac specification. Exposure to active FGF signaling in cardiac progenitors specifies SHF progenitor cells and cardiac fibroblasts (CFs). Human PSC-derived CFs retain many characteristics of primary CFs, including expression of biomarkers including GATA4, HAND2, HEY1, ISL1, NKX2-5, SOX17, BMP4, and WT1. The biomarkers GATA4, HAND2, HEY1, ISL1, NKX2-5, SOX17, BMP4, and WT1 show higher expression in hPSC-CFs than in primary CFs and the cytokine IL-6 shows reduced expression in hPSC-CFs. The chemically defined platform described here should be widely useful for generating functional cardiac fibroblasts for both research and clinical applications.

The CF differentiation process provided herein is chemically defined, and generates CFs from human pluripotent stem cells at a greater yield and lower cost than existing methods. In addition, these cells are suitable for translational applications since they can be derived in the absence of xenogeneic components. Since access to primary human CFs is limited by the scarcity of viable cardiac tissue, the methods provided herein have valuable applications such as inexpensive and reproducible generation of human CFs. Generating human CFs in chemically-defined conditions can facilitate translation of these cells to regenerative therapies and other clinical applications. As described in further detail below, the Inventors' protocols targeted key regulatory elements of the Wnt/β-catenin and FGF signaling pathways, simplifying the steps and components involved in deriving second heart field progenitors from pluripotent stem cells and deriving cardiac fibroblasts from the second heart field progenitors.

As used herein, the term "cardiac fibroblast" ("CF") refers to cells of the cardiac fibroblast lineage obtained in vitro according to a method provided herein. Cardiac fibroblasts are characterized and identified by expression of biomarkers including the transcription factors GATA4 (GATA Binding Protein 4) and HAND2 ("Heart And Neural Crest Derivatives Expressed 2"). GATA4 encodes a member of the GATA family of zinc-finger transcription factors. The GATA4 gene product plays a key role in cardiac development. As used herein, the term "biomarker" or "marker" refers to a biomolecule (e.g., protein, nucleic acid, carbohydrate, or lipid) that is differentially expressed in a cell in comparison to another cell type. Generally, biomarkers can be identified by, for example, gene expression analysis, including quantitative PCR, RT-PCR, RNA-Seq, Northern analysis, and in situ hybridization.

As used herein, the term "second heart field (SHF) progenitors" refers to cardiac progenitor cells obtained in vitro according to a method provided herein and that exhibit at least some properties of primary second heart field progenitors. SHF progenitors give rise to myocardium, smooth muscle, and endothelial cells, and can be identified based on expression of biomarkers such as TBX1 (also known as T-Box 1 and Brachyury), HAND2, and FGF10. In vivo, SHF progenitors are believed to be pharyngeal mesodermal progenitor cells that are situated medially to the primary or first heart field (FHF). While FHF progenitors contribute to the left ventricle, SHF progenitors contribute to the cardiac outflow tract (OFT), right ventricle, and inflow tract. During embryonic development, SHF progenitors contribute to growth of the elongating heart tube during looping morphogenesis. See, for review, Rochais et al., *Circ. Res.* 104:933-942 (2009).

In a first aspect, provided herein is a method for generating a population of human cardiac fibroblasts, where the method generally comprises culturing human pluripotent stem cells under conditions that promote differentiation of the hPSCs into second heart field progenitors and, ultimately, cardiac fibroblasts. As used herein, the phrases "differentiation into human cardiac fibroblast cells" and "differentiating into human cardiac fibroblast cells" refer to promoting the differentiation of iPS cells or human cardiac mesoderm progenitor cells into cells exhibiting the genetic markers, biomarkers, cell function, and/or cell morphology characteristic of a human cardiac fibroblast cell.

Preferably, the method comprises culturing human cardiac mesoderm progenitor cells in a chemically defined, also preferably yet optionally, xeno-free culture medium including a fibroblast growth factor (FGF), whereby a cell population including human cardiac fibroblast cells is obtained after about 16-24 days in culture (i.e., about 16, 17, 18, 19, 20, 21, 22, 23, or 24 days in culture). In one embodiment, the human cardiac mesoderm progenitor cells are cultured for 20 days.

As used herein, the term "fibroblast growth factor" or "FGF" refers to members of a family of growth factors involved in angiogenesis, wound healing, and embryonic development. FGFs are heparin-binding proteins and interactions with cell-surface-associated heparan sulfate proteoglycans have been shown to be essential for FGF signal transduction. FGFs are key players in the processes of proliferation and differentiation of wide variety of cells and tissues. There are several different FGF subfamilies, the member ligands of which include FGF1-FGF23. Of the known FGF ligands, all show some degree of overlap of receptor binding, with the exception of FGF11-FGF14.

In some embodiments, the FGF is selected from the group consisting of bFGF/FGF2, FGF4, FGF8, FGF10 and the mixtures thereof. While FGF2 has been primarily used in this stage, other factors, including FGF4, FGF8 or FGF10 can be used in place of FGF2. One may also use mixtures of two or more of FGF2, FGF4, FGF8 and FGF10 in this stage. In a specific embodiment, the FGF is FGF2.

In some embodiments, the effective concentration of FGF in the medium ranges from about 10 ng/ml to about 200 ng/ml. For example, the effective concentration of FGF may range from about 10 ng/ml to about 200 ng/ml, or from about 20 ng/ml to about 180 ng/ml, or about 30 ng/ml to about 170 ng/ml, or about 40 ng/ml to about 160 ng/ml, or about 50 ng/ml to about 150 ng/ml, or about 60 ng/ml to about 140 ng/ml, or about 70 ng/ml to about 130 ng/ml, or about 80 ng/ml to about 120 ng/ml. Preferably, the effective concentration of FGF ranges from about 25 ng/ml to about 125 ng/ml. More preferably, the effective concentration of FGF is about 75 ng/ml.

In some cases, the human cardiac mesoderm progenitor cells are obtained from a method involving culturing human pluripotent stem cells for about 2 to about 3 days in a chemically defined, albumin-free culture medium including an activator of Wnt/β-catenin signaling, whereby a cell population including cardiac mesodermal cells positive for expression of Brachyury/T is obtained.

As described herein, cells of the CF lineage can be generated without providing exogenous TGFβ superfamily growth factors such as Bone Morphogenetic Protein 4 (BMP4) and without generating epicardial cells as an intermediate cell type.

As will be appreciated by those of ordinary skill in the art, Wnt/β-catenin signaling can be activated by modulating the function of one or more proteins that participate in the Wnt/β-catenin signaling pathway to increase β-catenin expression levels or activity, TCF and LEF expression levels, or β-catenin/TCF/LEF induced transcriptional activity.

In some embodiments, Wnt/β-catenin signaling is activated by inhibiting Gsk3 phosphotransferase activity or Gsk3 binding interactions. While not wishing to be bound by theory, it is believed that inhibition of Gsk3 phosphorylation of β-catenin inhibits tonic degradation of β-catenin and thereby increases the β-catenin level and activity to drive pluripotent stem cell differentiation to an endodermal/mesodermal lineage. Gsk3 inhibition can be achieved in a variety of ways including, but not limited to, providing small molecules that inhibit Gsk3 phosphotransferase activity, RNA interference knockdown of Gsk3, and overexpression of dominant negative forms of Gsk3. Dominant negative forms of Gsk3 are known in the art as described, e.g., in Hagen et al. (2002), *J Biol Chem*, 277(26):23330-23335, which describes a Gsk3 including a R96A mutation.

In some embodiments, Gsk3 is inhibited by contacting a cell with a small molecule that inhibits Gsk3 phosphotransferase activity or Gsk3 binding interactions. Suitable small molecule Gsk3 inhibitors include, but are not limited to, CHIR99021, CHIR98014, BIO-acetoxime, BIO, LiCl, SB 216763, SB 415286, AR A014418, 1-Azakenpaullone, Bis-7-indolylmaleimide, and any combinations thereof. In some embodiments, any of CHIR99021, CHIR98014, and BIO-acetoxime are used to inhibit Gsk3 in pluripotent stem cells in the differentiation methods described herein. In one embodiment, the small molecule Gsk3 inhibitor is CHIR99021 at a concentration ranging from about 0.2 µM to about 20 µM, e.g., about 0.2 µM, 0.3 µM, 0.4 µM, 0.5 µM, 0.6 µM, 0.7 µM, 0.8 µM, 0.9 µM, 1 µM, 2 µM, 3 µM, 4 µM, 5 µM, 6 µM, 7 µM, 8 µM, 9 µM, 10 µM, 12 µM, 15 µM, 18 µM, 20 µM or another concentration of CHIR99021 from about 3 µM to about 20 µM. In another embodiment, the small molecule Gsk3 inhibitor to be used is CHIR98014 at a concentration ranging from about 0.1 µM to about 1 µM, e.g., about 0.1 µM, 0.2 µM, 0.3 µM, 0.4 µM, 0.5 µM, 0.6 µM, 0.7 µM, 0.8 µM, 0.9 µM or another concentration of CHIR98014 from about 0.1 µM to about 1 µM. In another embodiment, the small molecule Gsk3 inhibitor is BIO-acetoxime at a concentration ranging from about 0.1 µM to about 1 µM, e.g., about 0.1 µM, 0.2 µM, 0.3 µM, 0.4 µM, 0.5 µM, 0.6 µM, 0.7 µM, 0.8 µM, 0.9 µM or another concentration of BIO-acetoxime from about 0.1 µM to about 1 µM.

In other embodiments, Gsk3 activity is inhibited by RNA interference knockdown of Gsk3. For example, Gsk3 expression levels can be knocked-down using commercially available siRNAs against Gsk3, e.g., SignalSilence® GSK-3α/β(3 siRNA (catalog #6301 from Cell Signaling Technology®, Danvers, Mass.), or a retroviral vector with an inducible expression cassette for Gsk3, e.g., a commercially available Tet-inducible retroviral RNA interference (RNAi) system from Clontech (Mountain View, Calif.) Catalog No. 630926, or a cumate-inducible system from Systems Biosciences, Inc. (Mountain View, Calif.), e.g., the SparQ® system, catalog no. QM200PA-2.

In other embodiments, the Wnt/β-catenin signaling pathway is activated by overexpressing β-catenin itself, e.g., human β-catenin (exemplary nucleotide and amino acid sequences are found at GenBank Accession Nos: X87838 and CAA61107.1, respectively). In one embodiment, β-catenin overexpression is achieved using an inducible expression system, e.g., any of the just-mentioned inducible expression systems. Alternatively, a constitutively active, stabilized isoform of β-catenin is used, which contains point mutations S33A, S37A, T41A, and S45A as described, e.g., in Baba et al. (2005), Immunity 23(6):599-609.

In yet other embodiments, Wnt/β-catenin signaling pathway activation in pluripotent stem cells is achieved by contacting the cells with an agent that disrupts the interaction of β-catenin with Axin, a member of the β-catenin destruction complex. Disruption of the Axin/β-catenin interaction allows β-catenin to escape degradation by the destruction complex thereby increasing the net level of β-catenin to drive β-catenin signaling. For example, the Axin/β-catenin interaction can be disrupted in pluripotent cells by contacting the cells with the compound 5-(Furan-2-yl)-N-(3-(1H-imidazol-1-yl)propyl)-1,2-oxazole-3-carboxamide ("SKL2001"), which is commercially available, e.g., as catalog no. 681667 from EMD Millipore. An effective concentration of SKL2001 to activate Wnt/β-catenin signaling ranges from about 10 µM to about 100 µM, about 20 µM, 30 µM, 40 µM, 50 µM, 60 µM, 70 µM, 80 µM, 90 µM or another concentration of SKL2001 from about 10 µM to about 100 µM.

The methods provided herein produce populations of pluripotent stem cell-derived CFs, where the population is a substantially pure population of cardiac fibroblasts. As used herein, the term "substantially pure" refers to a population of cells that is at least about 75% (e.g., at least about 75%, 85%, 90%, 95%, 98%, 99% or more) pure, with respect to CFs making up a total cell population. In other words, the term "substantially pure" refers to a population of CFs of the present invention that contains fewer than about 20%, fewer than about 10%, or fewer than about 5% of non-cardiac fibroblast cells (e.g., cardiomyocytes) when directing differentiation to obtain cells of the CF lineage. The term "substantially pure" also refers to a population of CFs of the present invention that contains fewer than about 25%, about 10%, or about 5% of non-CFs in an isolated population prior to any enrichment, expansion step, or differentiation step. Typically, a population including CFs obtained by the disclosed methods comprises a very high proportion of CFs. In some embodiments, the cell population comprises about 50% to about 99% CFs, e.g., about 52%, 55%, 67%, 70%, 72%, 75%, 80%, 85%, 90%, 95%, 98%, or another percent of CFs from about 50% to about 99% CFs.

Cardiac fibroblasts can be identified by the presence of one or more CF markers. Useful gene expression or protein markers for identifying CFs include, without limitation, GATA4, HAND2, HEY1, ISL1, NKX2-5, and WT1 (Wilms tumor protein). Preferably, the method yields a cell population, at least 90% (e.g., at least 90%, 93%, 95%, 96%, 97%, 98%, 99% or more) of which are CFs positive for fibroblast marker (anti-human fibroblast antibody, clone TE-7, Millipore) and cardiac transcription factor GATA4, and negative for cardiomyocytes markers including MF20, cTnT. Molecular markers of CFs can be detected at the mRNA expression level or protein level by standard methods in the art. In some embodiments, no cell separation step or method is used to obtain a second cell population including at least 70% GATA4$^+$ cells or at least 85% GATA4$^+$ cells. In other embodiments, the proportion of CFs in a population of cells obtained in the described methods is enriched using a cell separation, cell sorting, or enrichment method, e.g., flow cytometry, fluorescence activated cell sorting (FACS), enzyme-linked immunosorbent assay (ELISA), magnetic beads, magnetic activated cell sorting (MACS), laser-targeted ablation of non-CF cells, and combinations thereof. Preferably, flow cytometry or FACS is used to identify and separate cells based on cell-surface antigen expression. In some embodiments, certain CF functional criteria are also assessed. Such functional cardiac fibroblast cell criteria include, without limitation, the ability to adhere and proliferate on tissue culture plastic (polystyrene) without coating, to migrate (for example, when assessed using a scratch assay), to generate cardiac-specific extracellular matrix proteins, and to form Cx43 based gap junctions with cardiomyocytes.

Each culturing step of the methods described herein is preferably performed under chemically defined and, also preferably yet optionally, xeno-free conditions. Chemically defined culture medium and substrate conditions for culturing pluripotent stem cells, as used in the methods described herein, are well known in the art. As used herein, the terms "chemically-defined culture conditions" and "fully-defined conditions" indicate that the identity and quantity of each medium ingredient is known and the identity and quantity of supportive surface is known. For purposes of this disclosure, "xeno-free" means having no xenogeneic products of non-human animal origin, such as cells, tissues and/or body fluids, or any tissue or blood components, such as non-human serum, which contain variable and undefined factors. The use of xeno-free medium and culture substrates reduces the risk of viral contamination or prion transmission. Accordingly, for human cells, a xeno-free culture medium is defined as a culture medium essentially free of non-human animal components.

In exemplary embodiments, human pluripotent stem cell-derived cardiac progenitor cells are singularized and replated at a low cell density in a basal culture medium. Optionally, such single cell replating is followed by a period of outgrowth before proceeding to activation of Wnt/β-catenin pathway signaling according to a method of generating CFs as provided herein.

As used herein, "pluripotent stem cells" appropriate for use according to a method of the invention are cells having the capacity to differentiate into cells of all three germ layers. Pluripotent stem cells (PSCs) suitable for the differentiation methods disclosed herein include, but are not limited to, human embryonic stem cells (hESCs), human induced pluripotent stem cells (hiPSCs), non-human primate embryonic stem cells (nhpESCs), non-human primate induced pluripotent stem cells (nhpiPSCs). As used herein, "embryonic stem cells" or "ESCs" mean a pluripotent cell or population of pluripotent cells derived from an inner cell mass of a blastocyst. See Thomson et al., Science 282:1145-1147 (1998). These cells express Oct-4, SSEA-3, SSEA-4, TRA-1-60, and TRA-1-81, and appear as compact colonies having a high nucleus to cytoplasm ratio and prominent nucleolus. ESCs are commercially available from sources such as WiCell Research Institute (Madison, Wis.).

As used herein, "induced pluripotent stem cells" or "iPS cells" mean a pluripotent cell or population of pluripotent cells that may vary with respect to their differentiated somatic cell of origin, that may vary with respect to a specific set of potency-determining factors and that may vary with respect to culture conditions used to isolate them, but nonetheless are substantially genetically identical to their respective differentiated somatic cell of origin and display characteristics similar to pluripotent stem cells, such as ESCs, as described herein. See, e.g., Yu et al., Science 318:1917-1920 (2007). Induced pluripotent stem cells exhibit morphological properties (e.g., round shape, large nucleoli and scant cytoplasm) and growth properties (e.g., doubling time of about seventeen to eighteen hours) akin to ESCs. In addition, iPS cells express pluripotent cell-specific markers (e.g., Oct-4, SSEA-3, SSEA-4, Tra-1-60, or Tra-1-81, but not SSEA-1). Induced pluripotent stem cells, however, are not immediately derived from embryos. As used herein, "not immediately derived from embryos" means that the starting cell type for producing iPS cells is a non-embryonic, non-pluripotent cell, such as a multipotent cell or terminally differentiated cell, such as somatic cells obtained from a post-natal individual.

Human iPS cells can be used according to a method described herein to obtain CFs having the genetic complement of a particular human subject. For example, it may be advantageous to obtain CFs that exhibit one or more specific phenotypes associated with or resulting from a particular disease or disorder of the particular mammalian subject. In such cases, iPS cells are obtained by reprogramming a somatic cell of a particular human subject according to methods known in the art. See, for example, Yu et al., Science 324(5928):797-801 (2009); Chen et al., Nat. Methods 8(5):424-9 (2011); Ebert et al., Nature 457(7227):277-80 (2009); Howden et al., Proc. Natl. Acad. Sci. U.S.A. 108(16):6537-42 (2011). Induced pluripotent stem cell-derived CFs allow modeling of drug responses in CFs obtained from an individual having, for example, a particular disease. Even the safest drugs may cause adverse reactions in certain individuals with a specific genetic background or environmental history. Accordingly, human subject-specific iPS cell-derived CFs are useful to identify genetic factors and epigenetic influences that contribute to variable drug responses.

Subject-specific somatic cells for reprogramming into iPS cells can be obtained or isolated from a target tissue of interest by biopsy or other tissue sampling methods. In some cases, subject-specific cells are manipulated in vitro prior to use. For example, subject-specific cells can be expanded, differentiated, genetically modified, contacted to polypeptides, nucleic acids, or other factors, cryo-preserved, or otherwise modified.

In some embodiments, pluripotent stem cells to be differentiated according to the methods disclosed herein are cultured in the presence of a serum-free, chemically-defined culture medium such as LaSR basal medium (a serum-free culture medium containing Advanced DMEM/F12, 2.5 mM GlutaMAX, and supplemented with 60 μg/mL ascorbic acid), mTESR-1® medium (StemCell Technologies, Inc., Vancouver, Calif.), or Essential 8® medium (Life Technologies, Inc.). A number of known basal culture media are suitable for use throughout the differentiation methods described herein. Such basal culture media include, but are not limited to, RPMI, DMEM/F12 (1:3), DMEM/F12 (1:1), DMEM/F12 (3:1), F12, DMEM, and MEM. In exemplary embodiments, these basal cell culture media are supplemented with 50 to 200 µg/ml L-Ascorbic acid 2-phosphate sesquimagnesium salt hydrate (e.g., Sigma, catalog no. A8960). For each differentiation step described herein, cells are cultured in a medium that is substantially free of exogenous Bone Morphogenetic Proteins (BMPs) such as BMP4.

In some cases, the basal culture medium is supplemented with suitable amounts of various components such as fatty acids or lipids, amino acids (such as non-essential amino acids), vitamin(s), growth factors, cytokines, antioxidant substances, 2-mercaptoethanol, pyruvic acid, buffering agents, inorganic salts, or serum such as fetal calf serum or autologous serum. Preferably, for being used in human therapy, the medium is serum-free, is supplemented with autologous serum, or contains an alternative to serum. From the aspect of preventing contamination with heterogeneous animal-derived components, serum can be derived from the same animal as that of the stem cell(s). Alternatives to serum can include materials which appropriately contain albumin (such as lipid-rich albumin, albumin substitutes such as recombinant albumin, plant starch, dextrans and protein hydrolysates), transferrin (or other iron transporters), fatty acids, insulin, collagen precursors, trace elements, 2-mercaptoethanol, 3'-thiolglycerol, or equivalents thereto. The alternatives to serum can be prepared by the method disclosed in International Publication No. 98/30679, for example. Alternatively, any commercially available materials can be used for more convenience. The commercially available materials include knockout Serum Replacement (KSR), Chemically-defined lipid concentrate (Gibco), and Glutamax (Gibco).

In some cases, cells to be differentiated according to the methods disclosed herein are cultured in the presence of an extracellular matrix (ECM) substrate or a substrate including one or more ECM proteins. Examples of ECM protein that may be useful in a substrate for the methods provided herein include laminin, collagen I, collagen IV, fibronectin, and vitronectin, by themselves or in various combinations. The ECM proteins may be of natural origin and purified from human or animal tissues. Alternatively, the ECM proteins may be genetically engineered recombinant proteins or synthetic in nature. The ECM proteins may be a whole protein or in the form of peptide fragments, native or engineered. In some cases, pluripotent stem cells to be differentiated according to the methods disclosed herein are cultured in the presence of a commercial product such as a Synthemax™ cell culture surface (Corning) or Matrigel™. In such cases, substrate materials can be coated onto tissue culture treated flasks and multi well plates. In certain aspects, Matrigel™ may be excluded from the cell culture. Matrigel™ is a gelatinous protein mixture secreted by mouse tumor cells and is commercially available from BD Biosciences (New Jersey, USA). In some embodiments, the pluripotent stem cells to be differentiated are cultured in the presence of an ECM substrate. In some embodiments, the human cardiac mesoderm progenitors are cultured in the presence of an ECM substrate. In some embodiments, the progenitors may be dissociated and replated on a solid substrate in the presence of Matrigel™.

In a further aspect, provided herein are compositions and methods for expanding a self-renewing population of human CFs for at least 10 population doublings. Preferably, the self-renewing population of human CFs are capable of being passaged at least 10, 11, 12, or 13 times, wherein the cells are non-senescent and are not immortalized. Therefore, provided herein is an expandable source of functional human cardiac fibroblast cells.

In a further aspect, provided herein is a co-culture generated using the cardiac fibroblast cells produced by the methods described herein. hPSC-CFs produced as described herein are co-cultured with hPSC-CMs to produce a model of cardiac functionality. The co-culture may comprise 100%, 95%, 90%, 80%, 70%, 60%, 50%, 40%, 30%, 25%, 20%, 15%, 10% or 5% CMs with the balance of the total cell population in the co-culture including CFs (i.e., when the co-culture comprises 90% CMs, total cell population comprises 10% CFs). Co-cultures of the present invention are plated in chemically defined medium at a density sufficient to form a monolayer. In some embodiments, the co-culture is cultured for about 7 days (i.e., about 4, 5, 6, 7, 8, 9, or 10 days). In one embodiment, cells are plated at a density of about 250,000 cells per 200 µl drop of medium. In some embodiments, the cells are plated at a density between about 50,000 cells per 200 µl drop and about 500,000 cells per 200 µl. In some embodiments, the cells are plated at a density of between about 60,000 cells/cm$^2$ and about 120,000 cells/cm$^2$ (i.e., about 60,000, about 70,000, about 80,000, about 90,000, about 100,000, about 110,000 or about 120,000 cells/cm$^2$). In some embodiments, the medium is EB20 (80% DMEM/F12, 0.1 mmol/L nonessential amino acids, 1 mmol/L 1-glutamine, 0.1 mmol/L β-mercaptoethanol, 20% FBS and 10 µmol/L blebbistatin), EB2 (RPMI plus 2% FBS), or RPMI (Invitrogen, Gibco) medium. In one embodiment, the medium is RPMI medium with B27 supplement. In some embodiments, the co-cultures are cultured in the presence of an extracellular matrix (ECM) substrate or a substrate including one or more ECM proteins.

The co-culture generated by the methods described herein may be used to assess or evaluate a number of functional parameters known in the art, including but not limited to, beating rate frequency, action potential duration, action potential shape, action potential conduction velocity, conduction pattern (reentry, rotors, fibrillatory) (Campbell et al., 2012 J Physiol, 590(24):6363-79; Hou et al., 2010 Circ Res., 107(12):1503-11; Kleber et al., Physiol Rev. 2004, 84(2): 431-88), intracellular calcium cycling, contraction, and metabolic fluxes. Any means known in the art for measuring or observing these functional parameters may be used. In some embodiments, these functional characteristics are measured by optical mapping. In some embodiments, intracellular calcium cycling is measured using fluorescent dyes including but not limited to Fura2 and Fluo4. In some embodiments, contraction is measured by video edge detection or matrix bead displacement. In some embodiments, metabolic flux and metabolic properties of the co-culture are measured using the Seahorse assay system.

The co-cultures of CFs and CMs described herein can be used to model cardiac arrhythmias by manipulating the ratio of CM to CF cells in the co-culture. In one embodiment, the co-culture comprises 10% hPSC-CFs and exhibits an increased beating rate frequency. In one embodiment, the co-culture comprises 50% hPCS-CFs and exhibits fibrillatory conduction. In some embodiments the co-cultures are used to model spontaneous rate, electrical impulse conduction velocity and patterns of conduction. In some embodiments, the co-cultures are electrically paced to control their rate.

In a further aspect, described herein are methods of using the CF and CM co-culture as a cardiac arrhythmia model to screen drug candidates for their efficacy inhibiting human cardiac arrhythmic behavior. In some embodiments, a co-culture of cardiac fibroblasts and cardiomyocytes are contacted with a test agent and the effect of the test agent on the co-culture is observed or measured. In some embodiments, cardiac fibroblast cells generated by the methods described herein are co-cultured with cardiomyocytes and labelled with a suitable fluorescent dye to quantify spontaneous electrical impulse propagation and other electrophysiological properties of the co-culture and the co-culture is contacted with a test agent. The co-culture may be contacted with the test agent for any amount of time. Following contact by the test agent, the spontaneous rate, electrical impulse conduction velocity and pattern of conduction as well as other electrophysiological properties (e.g., action potential duration) are measured and compared to the same properties measured in a co-culture which has not been contacted by the test agent. In some embodiments, the test agent may increase the impulse conduction velocity and/or increase the action potential duration to block the fibrillatory or reentry patterns of conduction indicating that the test agent is a candidate agent suitable for the treatment of cardiac arrhythmia. Modulation of the functional parameter after contacting the co-culture with the test agent will indicate the test agent's utility as a candidate therapeutic agent for the treatment of a cardiac arrhythmia. In some embodiments, an increase in the functional parameter will indicate that the test agent is a candidate therapeutic agent. In some embodiments, a decrease in the functional parameter will indicate that the test agent is a candidate therapeutic agent. In embodiments wherein the co-cultures are electronically paced, the change in the functional parameter may be different than those observed in the same co-culture with a spontaneous rate.

It is also envisioned that the co-cultures of the present invention may be used to screen for proarrhythmic effects of a test agent. In some embodiments, a test agent may be characterized as having cardiac toxicity when the test agent modulates the functional parameter away from physiologically acceptable conditions. In some embodiments, test agents may be screened for their influence on the prolongation of the QT interval, wherein test agents that prolong the QT interval will be considered agents with the potential to induce drug-induced long QT syndrome.

As used herein, "test agent," refers to a molecule assessed for its ability to alter a specific phenotypic endpoint. Examples of test agents include, but are not limited to, (i) organic compounds of molecular weight less than about 600 daltons; (ii) nucleic acids; (iii) peptides (including stapled peptides); (iii) polypeptides; and (iv) antibodies. In some embodiments, the test agent is a drug specifically targeted to cardiac fibroblast cells, cardiomyocytes, or both. In some embodiments, the test agent is a beta-adrenergic receptor blocker. In some embodiments, beta-adrenergic receptor blockers which can target receptors on both cardiac fibroblasts and cardiomyocytes will be tested to determine the antiarrhythmic efficacy.

Articles of Manufacture

In another aspect, provided herein is a chemically defined culture medium for the differentiation of human cardiac progenitors into CFs. The culture medium comprises (i) a fibroblast growth factor; (ii) glutamine, provided as L-glutamine or GlutaMAX; (iii) ascorbic acid; (iv) hydrocortisone hemisuccinate; (v) insulin; (vi) human serum albumin; (vii) linoleic acid; (viii) lecithin; and (ix) DMEM, high glucose. In some embodiments, the medium is xeno-free. In some embodiments, glutamine is provided as GlutaMAX.

In another aspect, provided herein is a kit for generating human CFs. In exemplary embodiments, the kit comprises (i) a culture medium suitable for differentiating human cardiac progenitor cells into CFs; (ii) an agent that activates Wnt signaling in human cardiac progenitor cells; (iii) a fibroblast growth factor; and (iv) instructions describing a method for generating human CFs, the method employing the culture medium, the agent, and the fibroblast growth factor. In some cases, a kit provided herein further comprises or alternatively comprises instructions describing methods for in vitro maintenance of human CFs obtained according to a method provided herein, where the method employs a culture medium suitable for maintaining human CFs and an agent that supports long-term maintenance of such CFs.

Unless defined otherwise, all technical and scientific terms used herein have the same meaning as commonly understood by one of ordinary skill in the art to which the invention pertains. Although any methods and materials similar to or equivalent to those described herein can be used in the practice or testing of the present invention, preferred methods and materials are described herein.

In describing the embodiments and claiming the invention, the following terminology will be used in accordance with the definitions set out below.

As used herein, "about" means within 5% of a stated concentration range or within 5% of a stated time frame, unless otherwise specified.

As used herein, "a medium consisting essentially of" means a medium that contains the specified ingredients and those that do not materially affect its basic characteristics.

The terms "defined culture medium," "defined medium," and the like, as used herein, indicate that the identity and quantity of each medium ingredient is known. The term "defined," when used in relation to a culture medium or a culture condition, refers to a culture medium or a culture condition in which the nature and amounts of approximately all the components are known. A culture, composition, or culture medium is "essentially free" of certain reagents, such as signaling inhibitors, animal components or feeder cells, when the culture, composition, and medium, respectively, have a level of these reagents lower than a detectable level using conventional detection methods known to a person of ordinary skill in the art or that these agents have not been extrinsically added to the culture, composition, or medium.

As used herein, "effective amount" means an amount of an agent sufficient to evoke a specified cellular effect according to the present invention.

The invention will be more fully understood upon consideration of the following non-limiting Examples. It is specifically contemplated that the methods disclosed are suited for pluripotent stem cells generally. All publications, patents, and patent applications disclosed herein are hereby incorporated by reference as if set forth in their entirety.

EXAMPLES

Example 1

Human Pluripotent Stem Cell-derived Cardiac Fibroblasts from Second Heart Field Progenitors In this Example, we demonstrate the derivation of second heart field progenitors and cardiac fibroblasts from directed differentiation of hPSCs, and the characterization of the hPSC derived CFs (hPSC-CFs) in comparison with human primary cardiac fibroblasts and dermal fibroblasts by morphology, gene expression and functional analysis. In addition, the functional assessment by the co-culture of hPSC-CMs and hPSC-CFs is also discussed.

Methods

Human Pluripotent Stem Cell Culture: Human iPSC line DF19-9-11T and ESC line H1 and H9-TnnT2-GFP were used in this study. Human PSCs were cultured on Matrigel™ (GFR, BD Biosciences) coated 6-well plates in either mTeSR1 (DF19-9-11T, H1) medium (WiCell) or E8 (H9-TnnT2-GFP) medium (WiCell). Cells were passaged using Versene solution (Invitrogen) every 4-5 days. Cells were washed with PBS and incubated with 1 ml/well Versene solution at 37° C. for 3 minutes, aspirating Versene solution and adding 1 ml/well mTeSR1 or E8 medium to gently pipette up and down to split into cell clusters. Cell clusters were pelleted by centrifugation at 1000 rpm for 3 minutes, and resuspended in mTeSR1™ or E8™ medium, and plated in 6-well plate at the split ratio 1:6 to 1:12.

Differentiation of hPSCs to cardiomyocytes using GiWi protocol: Human PSCs were dissociated with 1 ml/well Versene solution at 37° C. for 5 minutes, and seeded on Matrigel™ coated 6-well plates at the density of $1.5 \times 10^6$ cells/well in mTeSR1 medium supplemented with 10 μM ROCK inhibitor (Y-27632) (Tocris). Cells were cultured for 5-6 days in mTeSR1 medium until the cells reached 100% confluence when differentiation started (day 0). At day 0, the medium was changed to 2.5 ml RPMI+B27 without insulin (Invitrogen) and supplemented with 12 μM CHIR99021 (Tocris) and cells were treated in this medium for 24 hrs (day 1). At day 1, medium was changed to 3 ml RPMI+B27 without insulin and cells were cultured in this medium for 48 hrs (day 3). 72 hrs (day 3) after addition of CHIR99021, a combined medium was prepared by collecting 1.5 ml of medium from the wells and mixing with same volume of fresh RPMI+B27 without insulin medium and supplemented with 5 μM IWP2 (Tocris), and cells were treated with IWP2 in the medium for 48 hrs (day 5). The medium was changed to 3 ml RPMI+B27 without insulin at day 5. At day 7 the medium was changed to RPMI+B27 with insulin (Invitrogen), and the cells were fed every other day and cultured until day 20 for flow cytometry analysis.

Differentiation of hPSCs to cardiac fibroblasts: Human PSCs were dissociated with 1 ml/well Versene solution (Invitrogen) at 37° C. for 5 minutes, and seeded on Matrigel™ (GFR, BD Biosciences) coated 6-well plates at the density of $1.5 \times 10^6$ cells/well in mTeSR1 medium supplemented with 10 μM ROCK inhibitor (Y-27632) (Tocris). Cells were cultured for 5-6 days in mTeSR1 medium with medium change daily until the cells reached 100% confluence when differentiation started (day 0). At day 0, the medium was changed to 2.5 ml RPMI+B27 without insulin (Invitrogen) and supplemented with 12 μM CHIR99021 (Tocris) and cells were treated in this medium for 24 hrs (day 1). At day 1, medium was changed to 3 ml RPMI+B27 without insulin and cells were cultured in this medium for another day (day 2). At day 2, the medium was changed to 2.5 ml of the defined fibroblast culture medium (Table 1) supplemented with bFGF (WiCell). Methods using L-glutamine in place of GlutaMAX were also successful. Cells were fed every other day and cultured until day 20 for flow cytometry analysis and subculture of cardiac fibroblasts.

TABLE 1

Cardiac Fibroblast Differentiation Medium

| Components | Final concentration |
|---|---|
| DMEM, high glucose (4.5 g/L) | basal medium |
| HLL Supplement: HSA (human serum albumin), linoleic acid and lecithin | HSA: 500 μg/mL Linoleic Acid: 0.6 μM Lecithin: 0.6 μg/mL |
| Ascorbic Acid | 50 μg/mL |
| GlutaMAX | 7.5 mM |
| Hydrocortisone Hemisuccinate | 1.0 μg/mL |
| rh Insulin | 5 μg/mL |

Culture of human cardiac fibroblasts and dermal fibroblasts: The hPSC-differentiated cardiac fibroblasts (hPSC-CFs), primary cardiac fibroblasts (Lonza, NHCF-V) and primary dermal fibroblasts (healthy donors, 020a and 023a lines) were used in this study. hPSC-CFs at 20 days differentiation were dissociated with 0.05% Trypsin-EDTA (Invitrogen) and plated in 6-well uncoated plastic plates at the density of 300,000 cells/well in 2 ml of FibroGRO™ medium (Millipore EMD, SCMF001) plus 2% FBS (Invitrogen). The hPSC-CFs were fed every other day with 2 ml FibroGRO™ medium and passaged every 4-6 days using 0.05% Trypsin-EDTA. The plating density for passaging hPSC-CFs was 5,800 cells/cm$^2$. The primary human CFs were purchased from Lonza (NHCF-V, Human Cardiac Fibroblasts-Ventricular, CC-2904, lot number 0000401462). The NHCF-V were thawed in FGM-3 medium (Lonza, CC-4526) in uncoated T75 flasks at the density of 3,500 cells/cm$^2$. The cells were fed every other day with the FGM-3 medium, and were passaged every 4-6 days using 0.05% Trypsin-EDTA. The plating density for passaging NHCF-V was 3,500 cells/cm$^2$. The primary dermal fibroblasts (020a, 023a) were thawed in DMEM high glucose with GlutaMAX™ supplement (Invitrogen 10566-016) plus 10% FBS (Invitrogen 10437) in uncoated 6-well plates at the density of 1,900 cells/cm$^2$. The cells were fed every other day with the same medium as the thawing medium and were passaged every 6-8 days using 0.05% Trypsin-EDTA. The plating density for passaging hDFs was 1,900 cells/cm$^2$.

Flow Cytometry: Cells were detached from cell culture plates by incubation with 0.25% trypsin-EDTA (Invitrogen) plus 2% chick serum (Sigma) for 5 minutes at 37° C. Cells were vortexed to disrupt the aggregates followed by neutralization by adding equal volume of EB20 medium (Zhang et al., Circ Res. 2009). Cells were counted and 0.5-1 million cells were used as the sample size for labeling. Cells were fixed in 1% paraformaldehyde in a 37° C. water bath for 10 minutes in the dark. For labeling intracellular markers, cells were permeabilized in ice-cold 90% methanol for 30 minutes on ice. Cells were washed once in FACS buffer (PBS without Ca/Mg$_2^+$, 0.5% BSA, 0.1% NaN3), centrifuged and resuspended in about 50 μl FACS buffer with (for intracellular markers) or without 0.1% Triton X-100. For labeling surface markers, appropriate amounts of the conjugated antibodies were added according to the manufacturer's instruction to the cells in FACS buffer to make the final volume of 100 μl with FACS buffer, and incubated in the dark for 30 minutes at room temperature. Cells were washed once with 3 ml FACS buffer and resuspended in 300-500 μl FACS buffer for analysis. For labeling intracellular markers, the primary antibody was diluted in 50 μl sample FACS buffer plus 0.1% Triton X-100 (Sigma) and aliquoted to each sample for a total sample volume of 100 μl. Samples were incubated with the primary antibodies overnight at 4° C. (see Table 2). For the secondary antibody labeling, cells were washed once with 3 ml FACS buffer plus 0.1% Triton after the primary antibody labeling, centrifuged, and the supernatant was discarded, leaving ~50 μl. Secondary antibody specific to the primary IgG isotype was diluted in FACS buffer plus Triton X-100 (polyethylene glycol p-(1,1,3,3-tetramethylbutyl)-phenyl ether) in a final sample volume of 100 µl at 1:1000 dilution. Samples were incubated at room temperature for 30 minutes in the dark, washed in FACS buffer plus Triton X-100 and resuspended in 300-500 µl FACS buffer plus Triton X-100 for analysis. Data were collected on a FACSCalibur™ flow cytometer (Beckton Dickinson) and analyzed using FlowJo™ software.

TABLE 2

Primary Antibodies for Flow Cytometry and Immunocytochemistry

| Antibody | Supplier (cat#) | Species | Isotype | Concentration |
| --- | --- | --- | --- | --- |
| Human/Mouse Brachyury PE-conjugated | R&D (IC2085P) | Goat | IgG | 10 µl/1 × $10^6$ cells (FC) |
| FITC anti-human CD90 | Biolegend (328108) | Mouse | IgG1 | 5 µl/1 × $10^6$ cells (FC) |
| Human APLNR APC-conjugated | R&D (FAB856A) | Mouse | IgG3 | 3 µl/1 × $10^6$ cells (live labeling) (FC) |
| Alexa Fluor 647 Mouse Anti-Human CD309 (KDR) | BD (560495) | Mouse | IgG1 | 20 µl/1 × $10^6$ cells (FC) |
| PE Mouse Anti-Human CD140a (PDGFRα) | BD (556002) | Mouse | IgG2a | 20 µl/1 × $10^6$ cells (FC) |
| FITC Mouse Anti-Human CD31 | BD (560984) | Mouse | IgG1 | 20 µl/1 × $10^6$ cells (FC) |
| Anti-Feeder-APC (Clone mEF-SK4) | Miltenyi Biotec (130-102-302) | Rat | IgG1 | 1:10 dilution (FC) |
| Mouse Anti-Human Fibroblasts (Clone TE-7) | CBL271 | Mouse | IgG1 | 1:100 dilution (FC, ICC) |
| MF20 | DSHB | Mouse | IgG2b | 1:20 dilution (FC, ICC) |
| Troponin T, Cardiac Isoform Ab-1 (Clone 13-11) | ThermoFisher Scientific (#MS-295-P) | Mouse | IgG1 | 1:100 dilution (FC, ICC) |
| Anti-Smooth Muscle Myosin | Biomedical Technologies Inc. (BT-562) | Rabbit | IgG | 1:500 dilution (FC, ICC) |
| GATA4 (H-112) | Santa Cruz (sc-9053) | Rabbit | IgG | 1:200 dilution (ICC) |
| Anti-Fibroblast-specific Protein 1 (S100A4) | EMD Millipore (#ABF32) | Rabbit | IgG | 1:500 dilution (ICC) |
| Fibronectin (A-11) | Santa Cruz (sc-271098) | Mouse | IgG2b | 1:100 dilution (ICC) |
| COL1A (COL-1) | Santa Cruz (sc-59772) | Mouse | IgG1 | 1:100 dilution (ICC) |

Immunocytochemistry: For imaging with a microscope from the EVOS™ line of cell imaging systems (Life Technologies), cells were cultured in either 6-well or 12-well plates. Cells were fixed with 4% paraformaldehyde for 15 minutes at room temperature, and permeabilized using 0.2% Triton X-100. After permeabilization for about 1 hour at room temperature, cells were blocked with 5% non-fat dry milk (Bio-Rad) in 0.2% Triton X-100 solution and incubated for 2 hours at room temperature on a rotator followed by two washes with PBS. Primary antibodies (Table 2) were added in 1% BSA in PBS solution with 0.1% Triton X-100, and incubated overnight at 4° C. Cells were washed with 0.2% Tween 20 in PBS twice and 1X PBS twice. Secondary antibodies specific to the primary IgG isotype were diluted (1:1000) in the same solution as the primary antibodies and incubated at room temperature for one hour on a rotator in the dark. Cells were washed with 0.2% Tween 20 in PBS twice and 1X PBS twice. Nuclei were labeled with Hoechst or DAPI.

RT-PCR and quantitative RT-PCR: Cell samples were collected using 0.25% trypsin-EDTA (Invitrogen) to remove the cells from cell culture plates. Total RNA was purified using QIAGEN RNeasy® Mini kit. Possible genomic DNA contamination was removed by RNase-Free DNase Set (QIAGEN) with the RNeasy® columns, or by DNase I (Invitrogen) treatment for 15 minutes at room temperature. 500 ng of total RNA was used for an Oligo(dT)20—primed reverse transcription (RT) reaction using SuperScript™ III First-Strand Synthesis System (Invitrogen). Quantitative RT-PCR (Q-PCR) was performed using Taqman PCR Master Mix and Gene Expression Assays (Applied Biosystems) in triplicate for each sample and each gene. 0.5 µl of cDNA from the RT reaction was added as template for each Q-PCR reaction. The expression of genes of interest was normalized to that of GAPDH. RT-PCR was carried out using Platinum™ Taq DNA Polymerase (Invitrogen) or Gotaq Master Mix (Promega). PCR conditions included denaturation at 94° C. for 30 seconds, annealing at 60° C. for 30 seconds, and extension at 72° C. for 1 minute, for 35 cycles, with 72° C. extension for 7 minutes at the end. The RT-PCR reaction products were subjected to electrophoresis in 2% agarose. ACTB ((β-actin) was used as an endogenous control.

RNA-seq and data analysis: Cell samples were collected using 0.25% trypsin-EDTA (Invitrogen) to remove the cells from cell culture plates. Total RNA was purified using QIAGEN RNeasy® Mini kit. Possible genomic DNA contamination was removed by RNase-Free DNase Set (QIAGEN) with the RNeasy columns. Duplicates for each sample were submitted for RNA-seq. Total RNA was qualified with the Life Technologies Qubit fluorometer (Q32857) and Agilent Bioanalyzer (G2940CA). One-hundred nanograms of total RNA was used to prepare indexed cDNA libraries with the Ligation Mediated Sequencing (LM-Seq) protocol (Hou Z et al, Scientific Reports 5, 2015). Final indexed cDNA libraries were pooled with thirty uniquely indexed LM-Se$_d$ cDNA libraries per lane and sequenced on an Illumina HiSeq 2500 with a single 51-bp read and a 10-bp index read. Base-calling and detnultiplexing were performed using Casava (v1.8.2). Sequences were filtered and trimmed to remove low quality reads, adapters, and other sequencing artifacts. The remaining reads were aligned to 19084 Refseq genes extracted from the Illumina iGenomes reference, selecting only those with 'NM_' annotations. Bowtie (v 0.12.9) was used for alignment, allowing two mismatches in a 28 bp seed (Langmead et al., Genome Biol. 2009; 10:R25). Reads with more than 200 alignments were excluded from further analysis. RSEM (v1.2.3) was used to estimate isoform and relative gene expression levels (transcripts per million or "TPM") (Li et al., B'*BMC Bioinformatics*. 2011; 12:323).

Extracellular matrix production and confocal imaging: Confluent hPSC-CFs, primary human CFs, and dermal fibroblast were dissociated with TrypLE™ reagent (a reagent free of animal- and human-derived components; Thermo Fisher) and seeded onto 6-well plates at the density of 1.25×10$^6$ cells/well. Cells were grown for 10 days with medium change every other day. hPSC-CFs were grown with FibroGRO™ medium (Millipore EMD, SCMF001) plus 2% FBS (Invitrogen), primary human CFs (NHCF-V) were grown in FGM-3 medium (Lonza), and dermal fibroblasts were grown with DMEM high glucose with GlutaMAX™ supplement (Invitrogen) plus 10% FBS (Invitrogen) medium. On day 10, cells for imaging were fixed with 4% paraformaldehyde for 15 minutes at room temperature, and stored in PBS at 4° C. For a total collagen assay, cells were treated using a modified decellularization protocol by Schmuck et al., *Cardiovascular Engineering and Technology* 5(1):119-131 (2014). The extracellular matrix proteins including collagen and fibronectin were co-labeled with anti-COL1A (COL-1) (Santa Crutz Biotechnology, sc-59772) and anti-Fibronectin (A-11) (Santa Crutz Biotechnology, sc-271089) antibodies without permeabilization of the cells to examine the extracellular matrix using the immunolabeling protocol in the 'Immunocytochemistry' section. Cells were imaged using the confocal microscope (Leica TCS SP5 system).

Co-cultures of hPSC-CM and hPSC-CF or hPSC-CM and hDF: hPSC-CMs were cultured with either hPSC-CFs or hDFs at varying percentages: 100%, 90%, 70%, 50% or 0%. These co-cultures were plated at a density of 250,000 cells per 200 ul drop of EB20 (80% DMEM/F12, 0.1 mmol/L nonessential amino acids, 1 mmol/L 1-glutamine, 0.1 mmol/L β-mercaptoethanol, 20% FBS and 10 µmol/L blebbistatin) on 18×18 mm pieces of polydimethylsiloxane (PDMS) silicone sheeting (SMI; Saginaw, Mich.) coated with Matrigel™ (500 µg/mL, Corning) and grown for 3 days kept at 37° C. in 5% CO2[43]. At this point the medium was changed to RPMI (Gibco) supplemented with B27 (Gibco) and replaced every two days for 4 days prior to experimentation.

Figure 5:
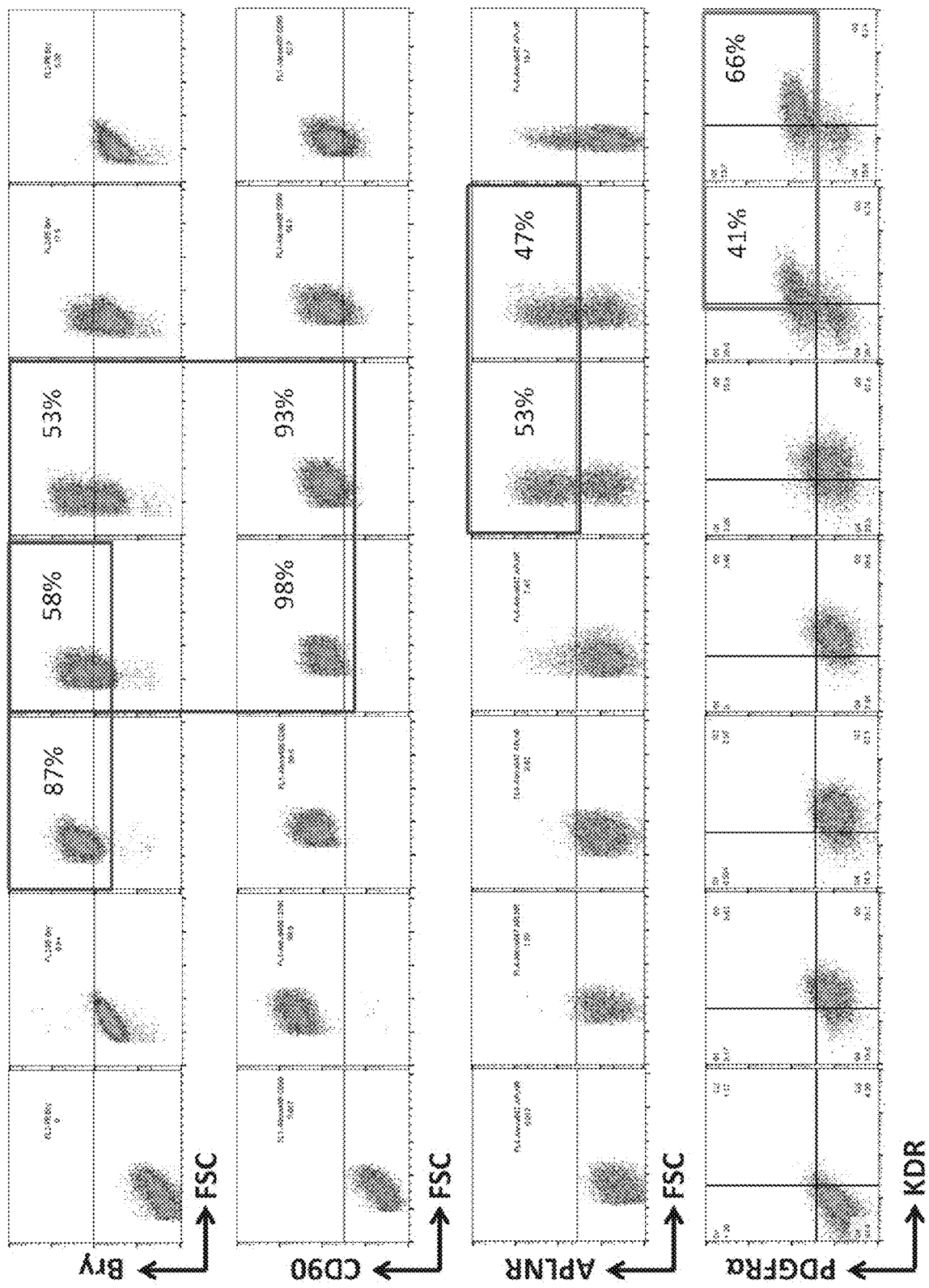
FIG. 5 presents flow cytometric analysis of stage specific progenitor cells in differentiation of human pluripotent stem cell line H1 at day 0-5 using the GiWi protocol. Images show cell surface expression of different progenitor stages. Colored boxes demonstrate pattern of gene expression in progenitors derived from H1 cell line. Green box: Brachyury positive early mesoderm. Red box: Brachyury low, CD90+. Purple box: APLNR+. Orange box: PDGFR-alpha/KDR positive progenitors.
Figure 6:
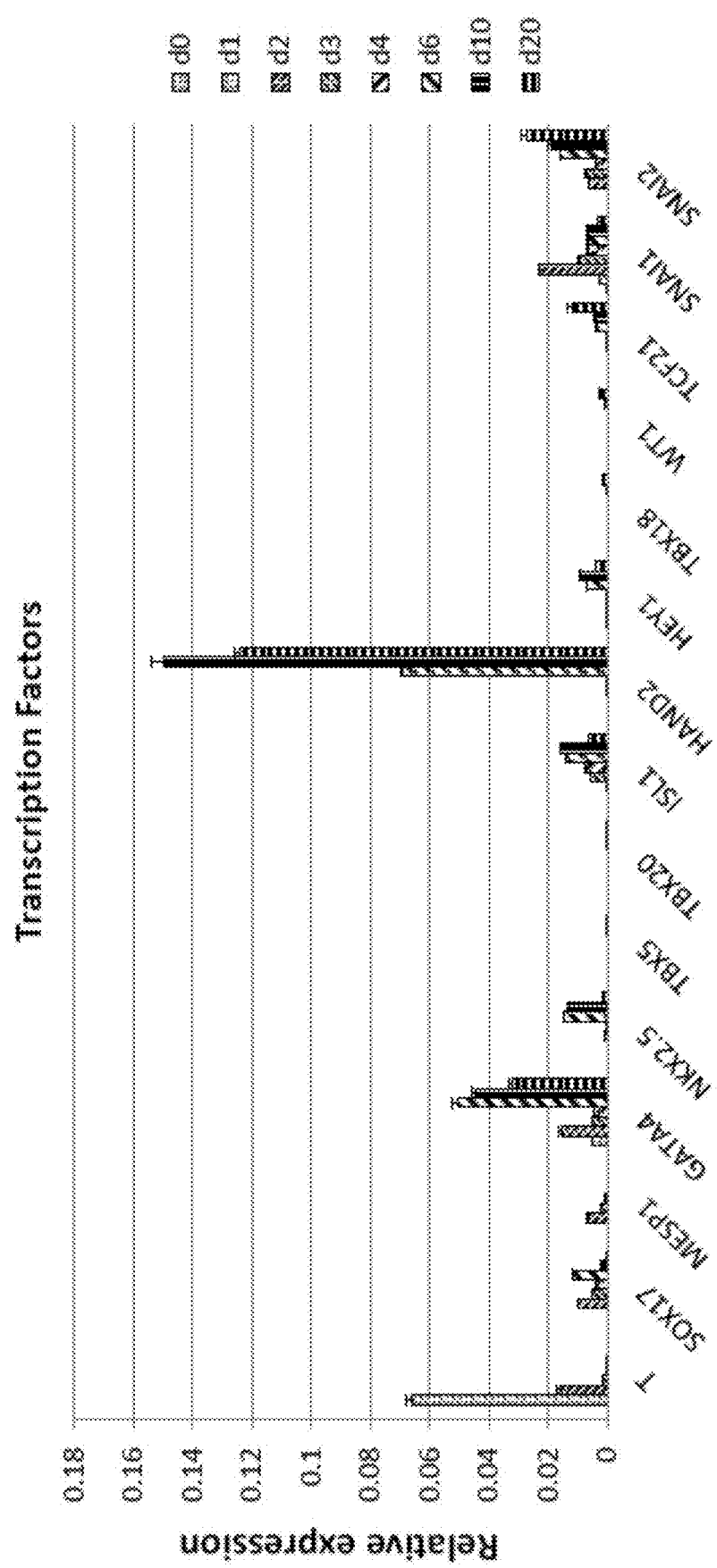
FIG. 6 presents quantitative RT-PCR of transcription factors in the time course (day 0-20) of cardiac fibroblast differentiation using the GiFGF protocol. Relative expression of each gene normalized to GAPDH is plotted.

Optical Mapping: Optical action potentials and time space plots were recorded using FluoVolt™ membrane potential probe (F10488, Life Technologies).[43-46] After a 30 minute incubation period, monolayers were transferred to Hank's balanced salt solution (HBSS with calcium and magnesium, Gibco) for optical mapping recording and kept at 37° C. for the duration of the experiment. All monolayers containing hPSC-CMs displayed spontaneous pacemaker activity which was recorded using a CCD camera (Red-Shirt Little Joe, Scimeasure, Decatur, Ga., 80×80 pixels) with the appropriate emission filters and LED illumination[44]. Ten second movies were taken at 200 fps (LabWindows Acquisition, National Instruments, Austin, Tex., USA) which were amplified, filtered and digitized for offline analysis. Movies were filtered in both the time and space domain and action potential duration (APD) and conduction velocity (CV) were measured as previously described[45, 46]. Repetitive stimuli (duration, 5 ms; strength, twice diastolic threshold) was applied by field stimulation using silver electrodes. Monolayers were paced faster than the spontaneous beating rate, which was different depending on the co-culture with hDFs or hPSC-CFs (FIGS. 5C-5D). Overlapping stimulation frequencies for each condition were obtained at cycle lengths of 400, 333.3 and 285.7 ms.

Statistics: Data are presented as mean±standard error of the mean (SEM). For datasets with normal distributions, statistical significance was determined by Student's t-test for two groups or one-way ANOVA for multiple groups with post-hoc test using Bonferroni and Tukey method. Statistical analysis was performed using Origin, v9, $P<0.05$ was considered statistically significant.

Results

During embryonic development, CFs arise starting at midgestation from multiple sources. The epicardium is the major source of CFs found in the ventricular myocardium with epicardial progenitors undergoing an epithelial to mesenchymal transition requiring expression of TCF21 to generate CFs[14-17]. In addition, another population of CFs has been identified in the heart derived from the endocardium at the time of endocardial cushion formation by an endothelial-to-mesenchymal transition[18, 19]. These endocardial-derived CFs contribute the cardiac valves and populate the interventricular septum to the greatest extent. Lastly, a small fraction of fibroblasts, mostly present in the right atrium, are derived from neural crest lineages[20]. Given that cardiac lineages are primarily derived from mesoderm, we hypothesized that manipulating cellular signaling impacting hPSC-derived mesodermal committed progenitors could efficiently lead to the generation of hPSC-CFs.

Biphasic modulation of the Wnt signaling pathway with small molecules is sufficient to direct the differentiation of monolayer cultured hPSCs to cardiomyocytes[21]. Activation of canonical Wnt signaling by GSK3β inhibition stimulates hPSCs to sequentially form mesoderm and cardiac progenitors that are subsequently induced to differentiate to cardiomyocytes by inhibition of Wnt signaling. We first determined the stage-specific mesodermal and cardiac progenitor populations generated by this small molecule (GiWi) protocol[22]. Flow cytometry demonstrated that the early mesodermal marker Brachyury was expressed in almost all cells after 24 hours of treatment with CHIR. Expression of Brachyury was present for another 24 hours before it was quickly downregulated after day 2 (FIGS. 1A-1B). CD90 was robustly expressed in hPSCs, but its expression gradually declined during the differentiation. Most of the cells expressed CD90 at days 2-3 (>80%) but the expression level of CD90 was relatively lower than in hPSCs (FIG. 1B). This Brachyury$^{down}$/CD90$^{low}$ progenitor stage first showed upregulation of MESP1 mRNA expression (FIG. 2B) which is expressed in cardiac mesodermal progenitors. The apelin receptor (APLNR) is expressed in early mesodermal progenitors importantly including lateral plate mesodermal cells specified to be cardiac progenitors as well as APLNR$^+$ cells that have the potential to give rise to mesenchymal stem cells (MSCs) and endothelial celld[23-26]. APLNR expression was first seen at day 3, and APLNR+ cells peaked at 66% of the cells on day 4 and then rapidly declined (FIG. 1B). KDR+/PDGFRα+ cells have been identified as cardiac progenitor cells (CPCs) that can be differentiated mainly to cardiomyocytes in the cardiac differentiation of hPSCs[11]. We found the KDR+/PDGFRα+CPCs were mainly generated on day 4-5 (FIGS. 1A-1B). These stage-specific progenitors were reproducibly generated from other hPSC lines using the GiWi protocol (FIG. 5)[22].

Because prior studies have demonstrated that FGF signaling contributes to the generation of cardiac mesodermal progenitors and exerts a dominant effect over BMP signaling directing cardiac mesodermal progenitors to nonmyocyte fates[27, 28], we tested the impact of FGF signaling on progenitors present following activation of canonical Wnt signaling by CHIR (FIG. 1C). Our goal was to bias the differentiation to generate cardiac fibroblasts rather than cardiomyocytes. We tested a range of concentrations of bFGF (0-125 ng/ml) in a defined medium for fibroblast growth (CFBM, Table 1) at different progenitor stages in the GiWi protocol (FIGS. 1C-1D). Following 20 days of differentiation, cells were analyzed by flow cytometry using a specific fibroblast antibody (mouse anti-human fibroblast, clone TE-7) and an antibody to sarcomeric myosin (MF20) expressed in cardiomyocytes. Changing the medium and adding bFGF on day 2 or day 3 effectively prevented the generation of MF20+ cardiomyocytes, and there was a concentration-dependent increase in fibroblast marker positive cells, which peaked at 75 ng/ml bFGF added on day 2 of differentiation (FIG. 1D). At higher concentration of bFGF when added on day 3 or day 4, significant cell death resulted after day 6 of differentiation and no cells survived at 20 days (FIG. 1D). Thus applying a fixed concentration of 75 ng/ml of bFGF to cardiac mesodermal progenitors in a context-dependent fashion generated large population of putative CFs in both the human iPS cell line DF19-9-11T and the ES cell line H1 (FIG. 1E).

Figures 2A, 2B, 2C:
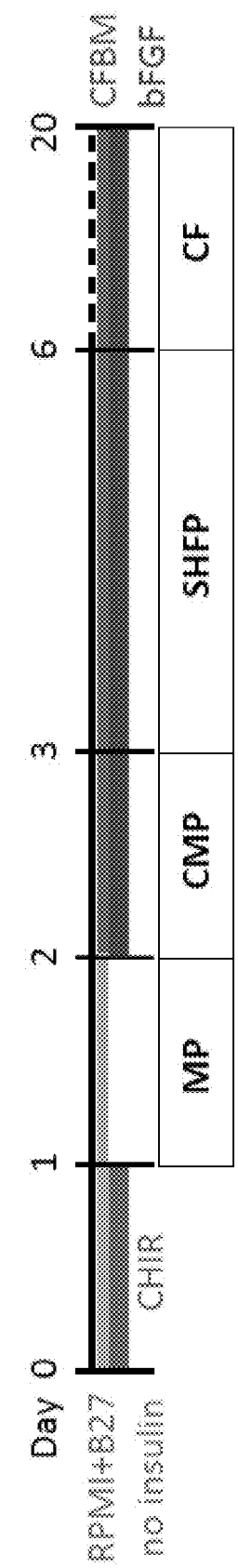
FIGS. 2A-2C demonstrate gene expression characterization of SHF progenitors and cardiac fibroblasts in the GiFGF protocol.
Figures 7A, 7B, 7C:
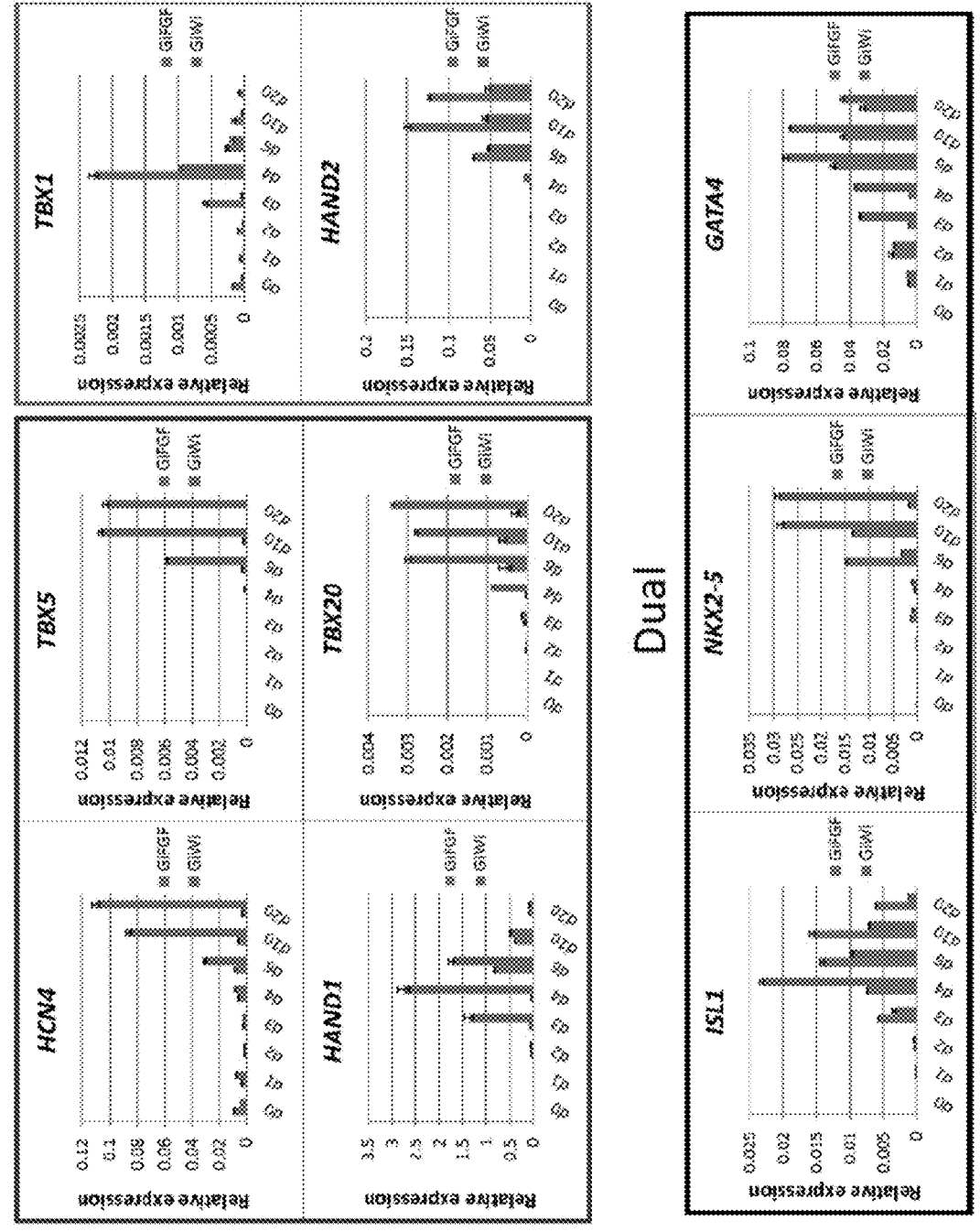
FIGS. 7A-7C show gene expression characterization in the cardiac fibroblast differentiation protocol—GiFGF, compared with the cardiomyocyte differentiation protocol—GiWi by qRT-PCR.

We refer to the protocol of adding 75 ng/ml of bFGF in CFBM medium starting on day 2 following GSK3β inhibition (Gi) as the GiFGF protocol (FIG. 2A). To understand the impact of bFGF on the differentiation of day 2 mesodermal progenitors in the GiFGF protocol, we examined the temporal gene expression pattern for developmentally regulated transcription factors and associated genes using quantitative RT-PCR (FIGS. 2A-2B; FIGS. 7A-7B). The early mesodermal gene T was transiently up-regulated after the GSK3β inhibitor (CHIR) treatment peaking at day 1, which is consistent with the transient expression of T during the primitive streak in development as well as the observations from other in vitro cardiac differentiation protocols[27, 29], and our flow cytometry data (FIG. 1B). MESP1 and GATA4 started to express on day 2 of differentiation following the expression of T, indicating onset of cardiac mesodermal progenitors. Next, the cardiac-related transcription factors were upregulated following bFGF treatment including ISL1, TBX1, GATA4, NKX2.5, HAND2 (FIG. 2B and FIGS. 7A-7B). The expression of ISL1, GATA4 and HAND2 remained high through 20 days of differentiation. Interestingly, the pattern of expression is consistent with the formation of second heart field (SHF) progenitors given the prominent expression of ISL1, TBX1, GATA4 and HAND2 [30-33]. These results contrast the cardiomyocyte-optimized GiWi protocol in which transcription factors associated with first heart field (FHF) progenitors including TBX5[34], HAND1 and TBX20 are more prominently expressed (FIG. 7A). In addition, the ion channel gene, HCN4, which is recognized as the FHF progenitor marker[35], is minimally expressed in the GiFGF protocol compared to the GiWi protocol (FIG. 2B and FIG. 7A). TCF21, a bHLH transcription factor required for the formation of CF in mouse heart[16], was progressively upregulated from day 6-20 in the GiFGF protocol (FIG. 2B and FIG. 7B). However, we did not observe a significant upregulation of epicardial progenitor genes such as TBX18 and WT1 in the FGF directed CFs differentiation (FIG. 2B and FIG. 7B), consistent with the findings that FGF signaling inhibited (pro) epicardium differentiation from the cardiac mesoderm[27]. We also examined the EMT markers of SNAI1 and SNAI2 in the GiFGF protocol and found an early upregulation of SNAP (day 2-3) and a late upregulation of SNAI2 (day 6-20) (FIG. 2B), consistent with their differential roles in promoting EMT [36], in which SNAP promotes mesoderm formation by downregulation of ectodermal gene expression, while SNAI2 represses E-cadherin expression during the EMT in CFs differentiation. VIM, a common fibroblast marker, was greatly upregulated during CF differentiation (FIG. 2C). In contrast, TNNT2, a typical cardiomyocyte marker, is minimally expressed in the GiFGF protocol (FIG. 2C). Furthermore, POSTN, a gene expressed in cardiac fibroblasts[37], was also greatly upregulated by 20 days differentiation in the GiFGF protocol, whereas the general fibroblast-associated DDR2 gene showed smaller fold change compared to POSTN (FIG. 2C). To screen for gene expression typical of endothelial or smooth muscle cells, we examined PECAM1 (CD31) and MYH11 (smooth muscle myosin heavy chain) expression and found there was very low expression of PECAM1 and essentially no expression of MYH11 in the GiFGF protocol (FIG. 2C). Finally, THY1 (CD90) expression was high in the undifferentiated stem cells, but downregulated during CFs differentiation (FIG. 2C). Given that high bFGF concentrations can be supportive of maintenance of pluripotency, we examined the expression of the pluripotency gene OCT4 and showed it to be completely downregulated during the CF differentiation (FIG. 2C), similar to the downregulation observed in cardiomyocyte differentiation protocols[12, 21, 29].

Figures 3A, 3B, 3C, 3D, 3E, 3F, 3G:
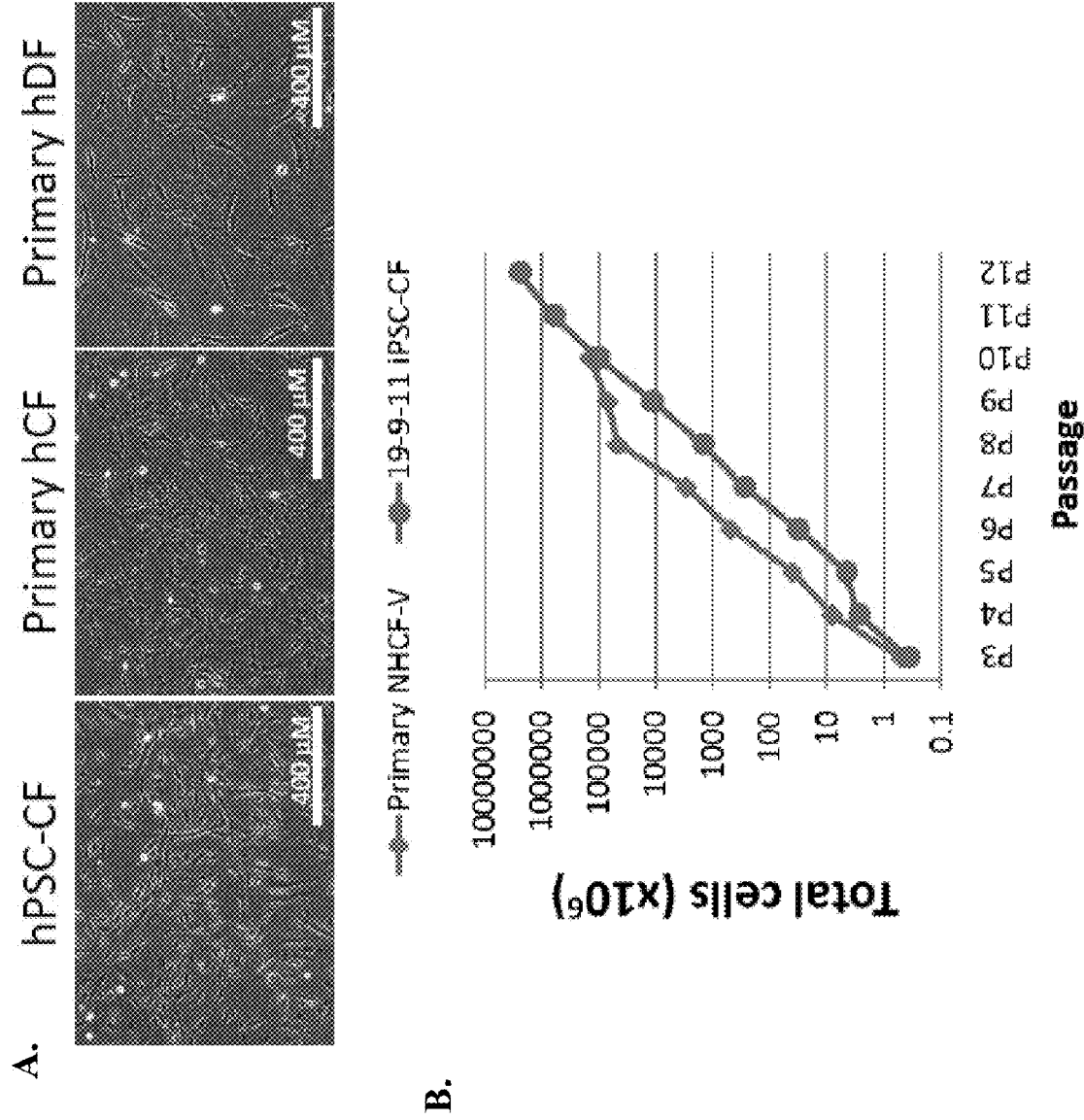
FIGS. 3A-3G demonstrates characterization of cardiac fibroblasts differentiated from human pluripotent stem cells (hPSC-CF) in comparison with primary cardiac fibroblast and dermal fibroblast.
Figure 8:
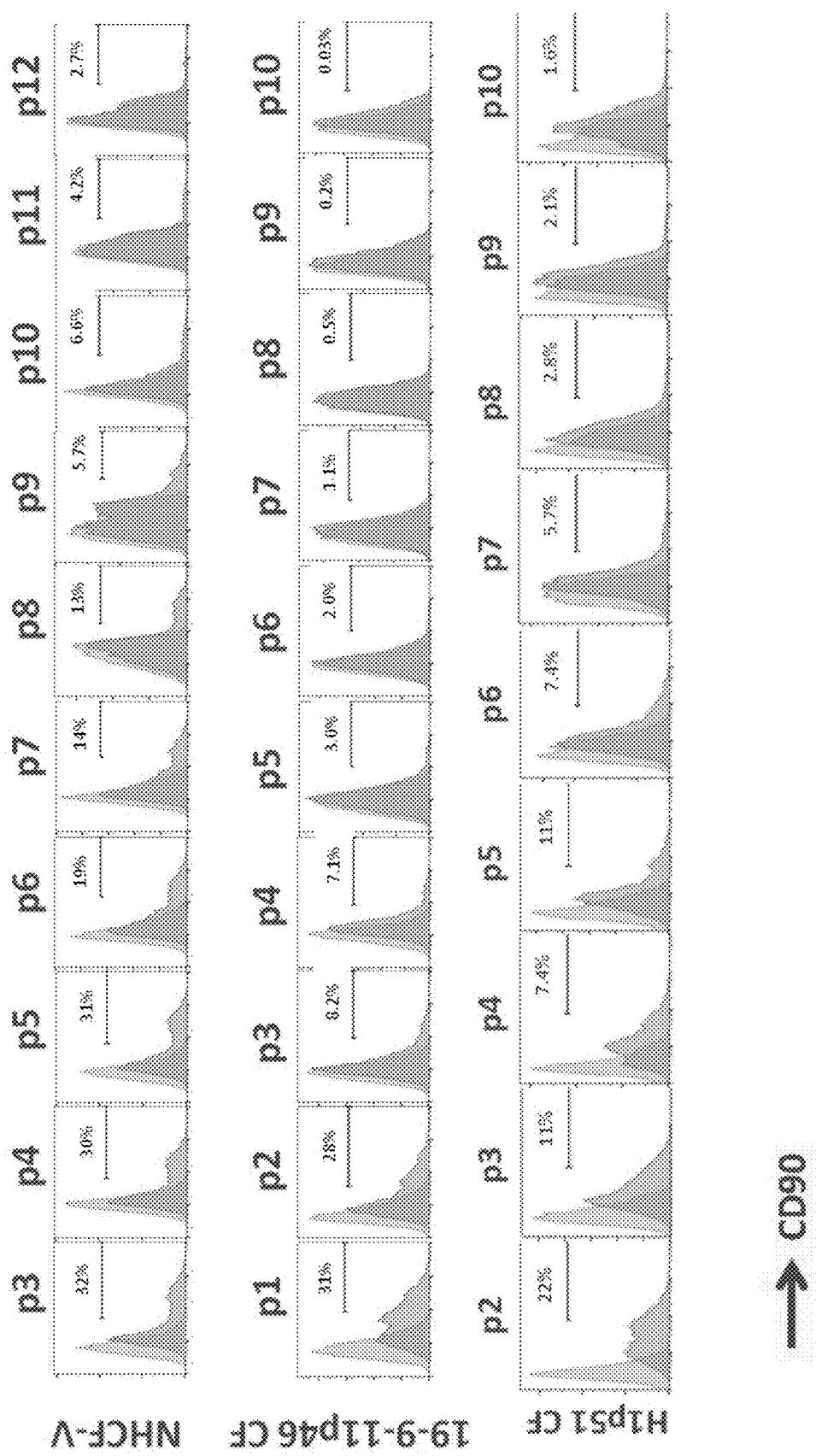
FIG. 8 presents flow cytometric analysis by histogram of CD90 expression in culture of human primary CF (NHCF-V), human iPSC differentiated CF (19-9-11p46 CF), H1p51 CF, human ESC differentiated CF (TnnT2p47 CF) and human primary dermal fibroblast (hDF (020a)) during passaging. P indicates passage. TnnT2 is a transgenic hES cell line from H9 containing the human cardiac specific troponin T gene (TNNT2) promoter driving expression of copGFP, the full name is H9-cTnT-GFP (Wrighton P J et al. PNAS 2014).
Figure 9:
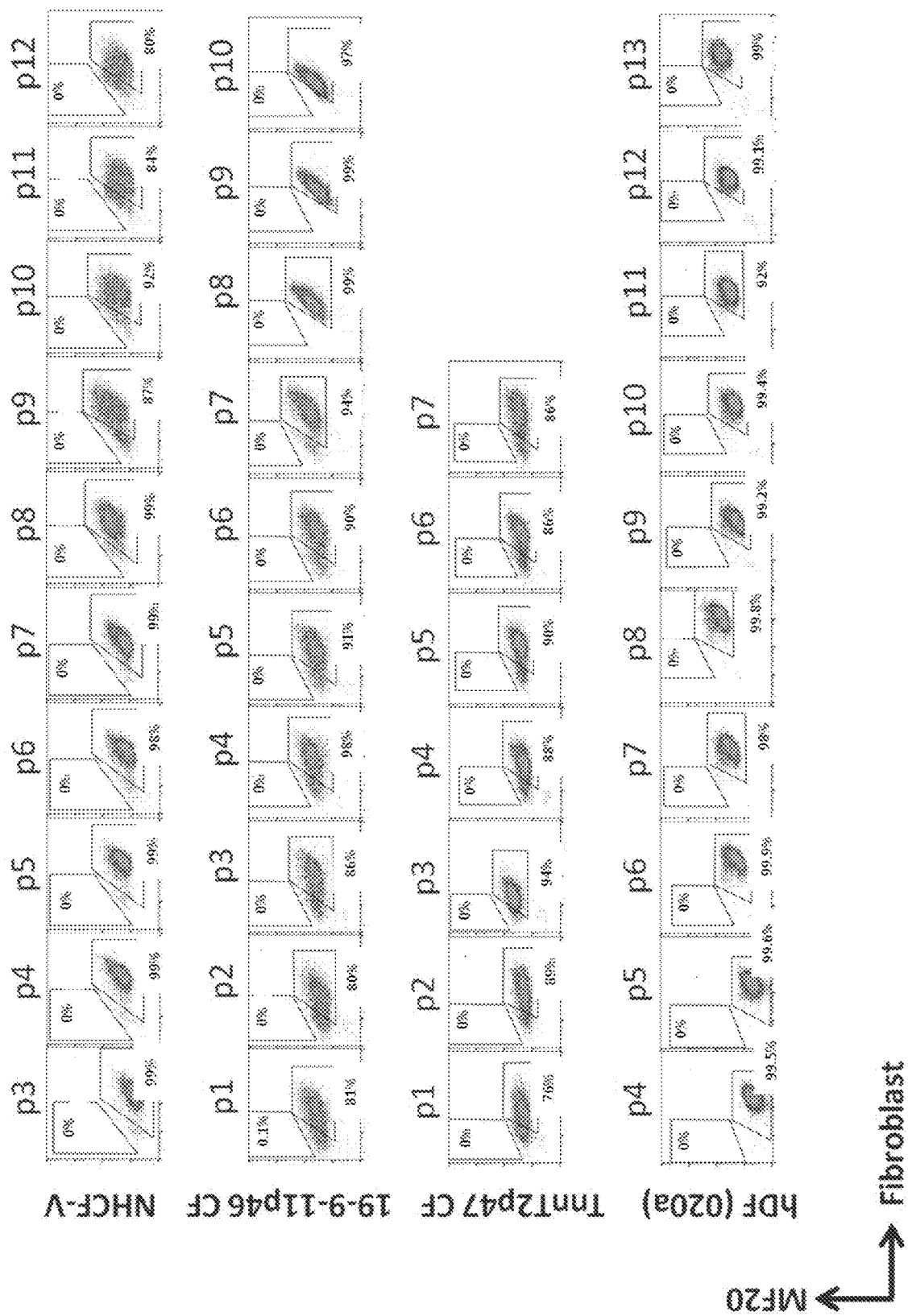
FIG. 9 presents flow cytometric analysis by dot plot of MF20 (anti-sarcomere myosin) and fibroblast (clone TE-7, anti-human fibroblast) expression in culture of human primary CF (NHCF-V), human iPSC differentiated CF (19-9-11p46 CF), human ESC differentiated CF (TnnT2p47 CF) and human primary dermal fibroblast (hDF (020a)) during passaging. P indicates passage.
Figures 10A, 10B, 10C, 10D:
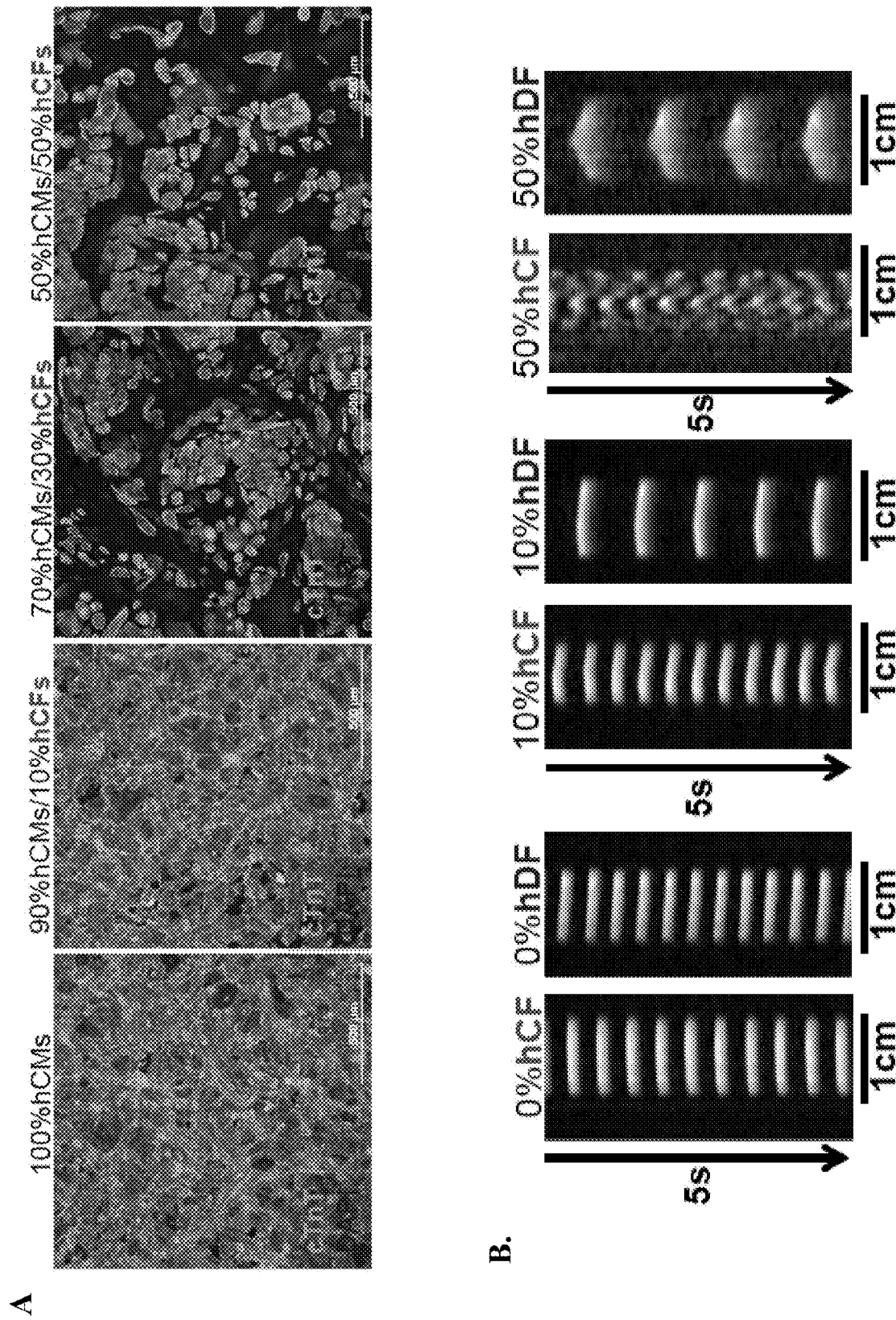
FIGS. 10A-10D show co-culture of hPSC-CMs with either hPSC-CFs or hDFs.
Figure 11:
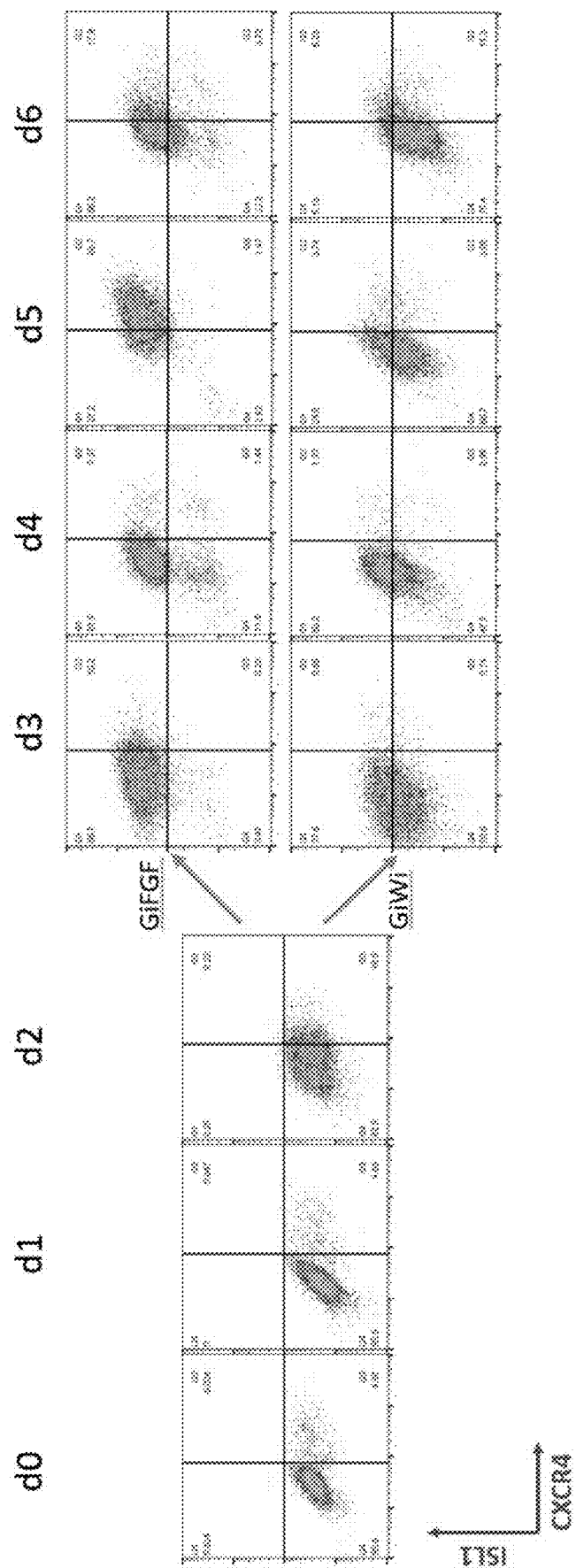
FIG. 11 shows flow cytometry of cells labeled with ISL1 and CXCR4 antibodies at progenitor stages in the differentiation into cardiac fibroblasts using the GiFGF protocol and differentiation into cardiomyocytes using the GiWi protocol as a comparison.

We next compared the properties of hPSC-CF populations with human primary adult cardiac fibroblasts (NHCF-V, Lonza) and dermal fibroblasts (hDF). The morphology of hPSC-CF, NHCF-V and hDF maintained in similar media was comparable with spindle-shaped and polygonal cells present (FIG. 3A). The hPSC-CF can propagate for at least 10 passages before undergoing senescence similar to primary CFs (FIG. 3B). The expression of CD90 (THY1), which has been used as a cell surface marker for some fibroblasts populations, was uniformly expressed on hDF and maintained over multiple passages (FIG. 3C and FIG. 8). In contrast, expression of CD90 was present on only a fraction of hPSC-CF or HNCF-V (22-40%) and was present on a progressively smaller percentage of cells with passaging. Notably, the hPSC-CFs and HNCF-V showed a similar change in expression of this surface marker over passages. The hDF were also uniformly positive for an intracellular fibroblast marker (clone TE-7)[38], and the hPSC-CF and NHCF-V showed that 65-90% of the cells were positive at early passage, and the purity increased to 75-99% with subsequent passaging (FIG. 3D and FIG. 9). Thus, the hPSC-CFs and NHCF-V populations share similar expression patterns of fibroblast markers over sequential passaging which is distinct from hDFs.

We also examined the cell preparations for markers of other related cell lineages including CD31 (endothelial), SM-MHC (smooth muscle) and MF20 (cardiomyocytes) by flow cytometry in comparison to the GiWi cardiomyocyte protocol. Unlike the GiWi protocol which generated MF20+ cardiomyocytes as the majority of cells, the GiFGF protocol produced very few MF20+ cardiomyocytes (0.8%) which became progressively less with passaging (FIG. 3E). A small ~5% SM-MHC+ population of cells was detected in the GiWi protocol, but a much smaller percentage was present with GiFGF which declined with passaging. None of the protocols produced clearly measurable numbers of CD31+ endothelial cells.

Immunolabeling of the cell preparations was performed to evaluate for other proteins associated with fibroblasts. Importantly, the TE-7-labeled fibroblasts from hPSC-CFs and NHCF-V were all GATA4 positive, which has been reported specifically in cardiac fibroblasts relative to fibroblasts from other tissues[7], but GATA4 was not detected in the primary hDF (FIG. 3F). There were no cTnT positive cardiomyocytes detected in any of the fibroblast cell lines (FIG. 3F). Immunolabeling for FSP1, another protein associated with fibroblasts, was detected in the majority of cells from all three preparations and likewise, the extracellular matrix proteins collagen I and fibronectin were expressed across the preparations (FIG. 3G). Thus, while hPSC-CFs share some properties with both hDFs and NHCF-V, they are most similar to NHCF-V in their marker expression and particularly in the expression of GATA4.

Figures 4A, 4B, 4C, 4D, 4E, 4F:
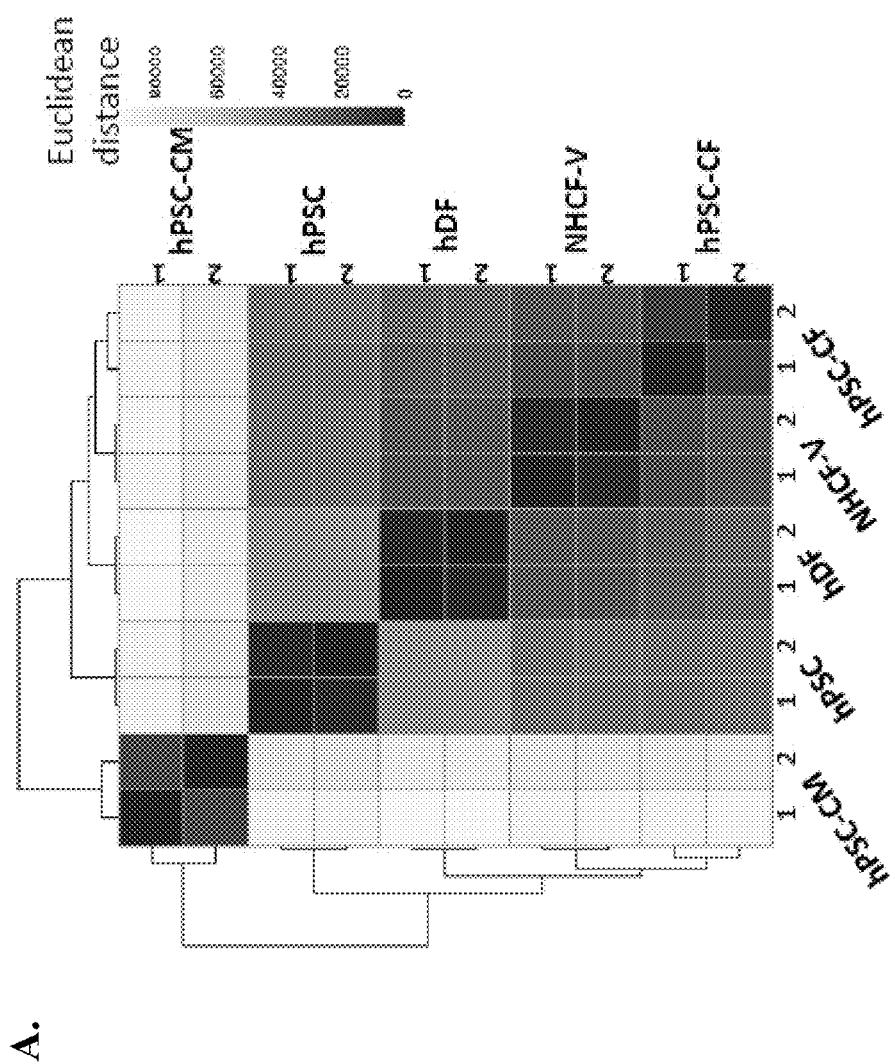
FIGS. 4A-4F demonstrate gene expression characterization of hPSC-CF, in comparison with NHCF-V hDF, hPSC-CM and hPSC by RNA-seq, and the 3D structure of ECM scaffolds from hPSC-CF, NHCF-V and hDF.

To characterize the gene expression pattern in hPSC-CFs, we performed RNA-seq on hPSC-CFs and compared the total mRNA transcripts with those of NHCF-V, hDF, hPSC-differentiated cardiomyocytes (hPSC-CM), and hPSC. Statistical analysis of gene expression across all the samples from the RNA-seq results showed the greatest similarity in the abundance of overall transcripts (19,084) between hPSC-CFs and primary CFs (NHCF-V) calculated by Euclidean distance (FIG. 4A). Gene Ontology analysis using the online tool AmiGO2 for cardiac-related genes (57) from the RNA-seq results demonstrated enriched cardiac factors in hPSC-CF, NHCF-V and hPSC-CM which clustered together relative to the hDF and hPSC samples (FIG. 4B). For example, hPSC-CF and NHCF-V showed relatively higher expression of BMP4, GATA4, HAND2, HEY1, ISL1, NKX2.5, SOX17 and WT1 relative to hDF (FIG. 4B). We also analyzed the ECM related gene expression in all samples given the importance of ECM production in fibroblast biology. High expression of collagen 1, 3, 4, 5, 6 and fibronectin, and the MMP2, 14, and TIMP2 was seen for all types of fibroblasts with hPSC-CF and NHCF-V clustering most closely (FIG. 4C). In summary, the RNA-seq data show that hPSC-CF and NHCF-V have the most similar gene expression pattern overall and specifically for cardiac-related genes and matrix genes.

Generation of ECM is a major function of CFs. Therefore, we examined the 3D structure of the ECM scaffolds generated by the hPSC-CF in comparison with the primary CF (NHCF-V) and hDF following 10 days of high-density culture[39]. The cultures were fixed and immunolabeled with anti-collagen IA and anti-human fibronectin antibodies, and nuclei were stained with Hoechst. Confocal imaging demonstrated that all three fibroblast preparations robustly produced collagen I and fibronectin (FIG. 4D). However, 3D reconstructions demonstrated that the hPSC-CF and NHCF-V produced multi-cell layer cultures while the hDF produced only monolayer cultures. This was also reflected in the greater thickness of the hPSC-CF CF (~35 μm) and NHCF-V cultures (~21 μm) relative to the hDF cultures (~10 μm) (FIG. 4E). Furthermore, both the hPSC-CF and NHCF-V resulted in polarized matrix production with fibronectin concentrated at the top of the culture in contrast to the hDF culture which showed fibronectin and collagen I labeling equivalently throughout the depth of the culture (FIG. 4D). Overall, the hPSC-CF in high-density culture generate an ECM scaffold in a similar fashion to NHCF-V which is distinct from that of hDF cultures.

Given that CFs can influence the electrophysiological properties of the native heart particularly in disease, we examined the functional impact of the co-culture of hPSC-CFs with hPSC-CMs, compared to the co-culture of hDFs with hPSC-CMs. Various ratios of hPSC-CMs and fibroblasts were co-cultured, and representative images confirm different co-culture proportions using immunofluorescent staining for cTnT (green) to label hPSC-CMs and DAPI to label the nuclei of all cells (FIG. 5A). In functional experiments, co-cultured monolayers were labelled with membrane potential dye (FluoVolt) to quantify electrophysiological effects of hPSC-CFs and hDFs on the spontaneous electrical impulse propagation. Time-space plots of action potential propagation (FIG. 5B) show the differential impact of each fibroblast subtype on hPSC-CM monolayer function. The presence of 10% hDFs decreased the spontaneous rate of cardiac monolayers by more than 50% relative to 100% hPSC-CMs, whereas 10% hCF did not have significant effect on the spontaneous rate. Impulse conduction velocity was slowed significantly with 10% of either type of fibroblast, although to a greater extent in the hDF co-culture (FIGS. 5B-5C). Interestingly, at a ratio of 50% hPSC-CMs: 50% hPSC-CFs, we observed fibrillatory conduction patterns in all of the monolayer co-cultures tested (6/6) while the same ratio using hDFs did not induce this arrhythmia pattern in any monolayer co-cultures tested (0/6) (FIGS. 5B-5C). To match the electrical activation rate for each condition, we used field stimulation and constructed APD restitution curves for the monolayer co-cultures. 10% hDF monolayer co-cultures had significantly longer APD80 than 10% hPSC-CF monolayer co-cultures when pacing rate was matched (cycle lengths 400, 333.3 and 287.5 ms). These data suggest that hDF and hPSC-CFs have distinct influence on hPSC-CM monolayer function, consistent with tissue-specific fibroblast functional properties.

Overall, our data demonstrate that hPSCs can be efficiently differentiated to CFs by sequential activation of Wnt and FGF signaling to promote mesodermal, cardiac mesodermal and SHF progenitors leading to the efficient generation of CFs. The hPSC-CFs share characteristics with native CFs based on gene expression, matrix production and the distinct modulation of hPSC-CM electrophysiology. Access to an unlimited supply of hPSC-CFs will empower research in heart development and disease modeling, as well as efforts in drug discovery and tissue engineering.

REFERENCES—All publications, including but not limited to patents and patent applications, cited below are herein incorporated by reference as though set forth in their entirety in the present application.

1. Zeisberg, E. M. & Kalluri, R. Origins of cardiac fibroblasts. Circ Res 107, 1304-1312 (2010).
2. Lajiness, J. D. & Conway, S. J. The dynamic role of cardiac fibroblasts in development and disease. J Cardiovasc Transl Res 5, 739-748 (2012).
3. Souders, C. A., Bowers, S. L. & Baudino, T. A. Cardiac fibroblast: the renaissance cell. Circ Res 105, 1164-1176 (2009).
4. Camelliti, P., Borg, T. K. & Kohl, P. Structural and functional characterisation of cardiac fibroblasts. Cardiovasc Res 65, 40-51 (2005).

5. Porter, K. E. & Turner, N. A. Cardiac fibroblasts: at the heart of myocardial remodeling. Pharmacol Ther 123, 255-278 (2009).
6. Brown, R. D., Ambler, S. K., Mitchell, M. D. & Long, C. S. The cardiac fibroblast: therapeutic target in myocardial remodeling and failure. Annu Rev Pharmacol Toxicol 45, 657-687 (2005).
7. Furtado, M. B. et al. Cardiogenic genes expressed in cardiac fibroblasts contribute to heart development and repair. Circ Res 114, 1422-1434 (2014).
8. Ieda, M. et al. Cardiac fibroblasts regulate myocardial proliferation through beta 1 integrin signaling. Developmental cell 16, 233-244 (2009).
9. D'Souza, K. M. et al. G protein-coupled receptor kinase-2 is a novel regulator of collagen synthesis in adult human cardiac fibroblasts. J Biol Chem 286, 15507-15516 (2011).
10. Kohl, P. & Gourdie, R. G. Fibroblast-myocyte electrotonic coupling: does it occur in native cardiac tissue? J Mol Cell Cardiol 70, 37-46 (2014).
11. Kattman, S. J. et al. Stage-specific optimization of activin/nodal and BMP signaling promotes cardiac differentiation of mouse and human pluripotent stem cell lines. Cell Stem Cell 8, 228-240 (2011).
12. Zhang, J. et al. Extracellular matrix promotes highly efficient cardiac differentiation of human pluripotent stem cells: the matrix sandwich method. Circ Res 111, 1125-1136 (2012).
13. Witty, A. D. et al. Generation of the epicardial lineage from human pluripotent stem cells. Nat Biotechnol 32, 1026-1035 (2014).
14. Cai, C. L. et al. A myocardial lineage derives from Tbx18 epicardial cells. Nature 454, 104-108 (2008).
15. Smith, C. L., Baek, S. T., Sung, C. Y. & Tallquist, M. D. Epicardial-derived cell epithelial-to-mesenchymal transition and fate specification require PDGF receptor signaling. Circ Res 108, e15-26 (2011).
16. Acharya, A. et al. The bHLH transcription factor Tcf21 is required for lineage-specific EMT of cardiac fibroblast progenitors. Development 139, 2139-2149 (2012).
17. Mikawa, T. & Gourdie, R. G. Pericardial mesoderm generates a population of coronary smooth muscle cells migrating into the heart along with ingrowth of the epicardial organ. Dev Biol 174, 221-232 (1996).
18. Wessels, A. et al. Epicardially derived fibroblasts preferentially contribute to the parietal leaflets of the atrioventricular valves in the murine heart. Dev Biol 366, 111-124 (2012).
19. Moore-Morris, T. et al. Resident fibroblast lineages mediate pressure overload-induced cardiac fibrosis. J Clin Invest 124, 2921-2934 (2014).
20. Ali, S. R. et al. Developmental heterogeneity of cardiac fibroblasts does not predict pathological proliferation and activation. Circ Res 115, 625-635 (2014).
21. Lian, X. et al. Robust cardiomyocyte differentiation from human pluripotent stem cells via temporal modulation of canonical Wnt signaling. Proceedings of the National Academy of Sciences of the United States of America 109, E1848-1857 (2012).
22. Lian, X. et al. Directed cardiomyocyte differentiation from human pluripotent stem cells by modulating Wnt/beta-catenin signaling under fully defined conditions. Nat Protoc 8, 162-175 (2013).
23. Vodyanik, M. A. et al. A mesoderm-derived precursor for mesenchymal stem and endothelial cells. Cell Stem Cell 7, 718-729 (2010).
24. Zeng, X. X., Wilm, T. P., Sepich, D. S. & Solnica-Krezel, L. Apelin and its receptor control heart field formation during zebrafish gastrulation. Developmental cell 12, 391-402 (2007).
25. Scott, I. C. et al. The g protein-coupled receptor agtrl 1b regulates early development of myocardial progenitors. Developmental cell 12, 403-413 (2007).
26. D'Aniello, C. et al. G protein-coupled receptor APJ and its ligand apelin act downstream of Cripto to specify embryonic stem cells toward the cardiac lineage through extracellular signal-regulated kinase/p70S6 kinase signaling pathway. Circ Res 105, 231-238 (2009).
27. Loh, K. M. et al. Mapping the Pairwise Choices Leading from Pluripotency to Human Bone, Heart, and Other Mesoderm Cell Types. Cell 166, 451-467 (2016).
28. van Wijk, B. et al. Epicardium and myocardium separate from a common precursor pool by crosstalk between bone morphogenetic protein- and fibroblast growth factor-signaling pathways. Circ Res 105, 431-441 (2009).
29. Yang, L. et al. Human cardiovascular progenitor cells develop from a KDR+ embryonic-stem-cell-derived population. Nature 453, 524-528 (2008).
30. Cai, C. L. et al. Isl1 identifies a cardiac progenitor population that proliferates prior to differentiation and contributes a majority of cells to the heart. Dev.Cell 5, 877-889 (2003).
31. Xu, H. et al. Tbx1 has a dual role in the morphogenesis of the cardiac outflow tract. Development 131, 3217-3227 (2004).
32. Bu, L. et al. Human ISL1 heart progenitors generate diverse multipotent cardiovascular cell lineages. Nature 460, 113-117 (2009).
33. Tsuchihashi, T. et al. Hand2 function in second heart field progenitors is essential for cardiogenesis. Dev Biol 351, 62-69 (2011).
34. Bruneau, B. G. et al. Chamber-specific cardiac expression of Tbx5 and heart defects in Holt-Oram syndrome. Dev Biol 211, 100-108 (1999).
35. Spater, D. et al. A HCN4+ cardiomyogenic progenitor derived from the first heart field and human pluripotent stem cells. Nat Cell Biol 15, 1098-1106 (2013).
36. Villarejo, A., Cortes-Cabrera, A., Molina-Ortiz, P., Portillo, F. & Cano, A. Differential role of Snail 1 and Snail2 zinc fingers in E-cadherin repression and epithelial to mesenchymal transition. J Biol Chem 289, 930-941 (2014).
37. Snider, P. et al. Origin of cardiac fibroblasts and the role of periostin. Circ Res 105, 934-947 (2009).
38. Kaaya, E. E. et al. Heterogeneity of spindle cells in Kaposi's sarcoma: comparison of cells in lesions and in culture. J Acquir Immune Defic Syndr Hum Retrovirol 10, 295-305 (1995).
39. Schmuck, E. G. et al. Cardiac fibroblast-derived 3D extracellular matrix seeded with mesenchymal stem cells as a novel device to transfer cells to the ischemic myocardium. Cardiovascular engineering and technology 5, 119-131 (2014).
40. Zhang, J. et al. Functional cardiomyocytes derived from human induced pluripotent stem cells. Circ Res 104, e30-41 (2009).
41. Langmead, B., Trapnell, C., Pop, M. & Salzberg, S. L. Ultrafast and memory-efficient alignment of short DNA sequences to the human genome. Genome Biol 10, R25 (2009).
42. Li, B. & Dewey, C. N. RSEM: accurate transcript quantification from RNA-Seq data with or without a reference genome. BMC Bioinformatics 12, 323 (2011).

43. Herron, T. J. et al. Extracellular Matrix-Mediated Maturation of Human Pluripotent Stem Cell-Derived Cardiac Monolayer Structure and Electrophysiological Function. Circulation. Arrhythmia and electrophysiology 9, e003638 (2016).
44. Lee, P. et al. Single-sensor system for spatially resolved, continuous, and multiparametric optical mapping of cardiac tissue. Heart Rhythm 8, 1482-1491 (2011).
45. Morley, G. E. et al. Characterization of conduction in the ventricles of normal and heterozygous Cx43 knockout mice using optical mapping. J Cardiovasc Electrophysiol 10, 1361-1375 (1999).
46. Zaitsev, A. V., Berenfeld, O., Mironov, S. F., Jalife, J. & Pertsov, A. M. Distribution of excitation frequencies on the epicardial and endocardial surfaces of fibrillating ventricular wall of the sheep heart. Circ Res 86, 408-417 (2000).

The present invention has been presented by way of illustration and is not intended to be limited to the disclosed embodiments. Accordingly, those skilled in the art will realize that the invention is intended to encompass all modifications and alternative arrangements within the spirit and scope of the invention as set forth in the appended claims.

We claim:

1. A method for generating a population of human GATA4+ FSP1+ collagen I+ fibronectin+ ISL1+ HAND2+ TCF21+ SNAI2+ cells that bind antibody TE-7, the method comprising:
   a) culturing human pluripotent cells in chemically defined culture medium comprising a Gsk3 inhibitor for about 1 day such that a population of T+ SNAI2− cells forms;
   b) culturing the T+ SNAI2− cells in the chemically defined culture medium without the Gsk3 inhibitor for about 1 day such that a population of T+ MESP1+ GATA4+ SNAI1+ SNAI2+ cells forms, and
   c) culturing the T+ MESP1+ GATA4+ SNAI1+ SNAI2+ cells in a chemically defined culture medium free of exogenous Bone Morphogenetic Proteins (BMPs) and comprising a fibroblast growth factor for about 18 days such that a population of human GATA4+ FSP1+ collagen I+ fibronectin+ ISL1+ HAND2+ TCF21+ SNAI2+ cells that bind antibody TE-7 is generated.

2. The method of claim 1, wherein the fibroblast growth factor is FGF2.

3. The method of claim 1, wherein at least 90% of cells generated in step (c) bind antibody TE-7.

4. The method of claim 1, wherein the method does not comprise a cell separation or selection step.

5. The method of claim 1, wherein the human GATA4$^+$ FSP1$^+$ collagen I$^+$ fibronectin$^+$ ISL1$^+$ HAND2$^+$ TCF21$^+$ SNAI2$^+$ cells that bind antibody TE-7 are capable of undergoing at least 10 cell divisions.

6. The method of claim 1, wherein the Gsk3 inhibitor is one or more of CHIR99021, CHIR98014, BIO-acetoxime, BIO, LiCI, SB216763, SB415286, AR A014418, 1-Azakenpaullone, and Bis-7-indolylmaleimide.

7. The method of claim 6, wherein the Gsk3 inhibitor is CHIR99021 and is present in a concentration of about 0.2 µM to about 20 µM.

8. The method of claim 7, wherein the Gsk3 inhibitor is CHIR99021 and is present in a concentration of about 12 µM.

* * * * *